(12) United States Patent
Belyaev

(10) Patent No.: US 7,226,781 B1
(45) Date of Patent: Jun. 5, 2007

(54) CHAPERONE EXPRESSION GENOMES

(76) Inventor: Alexander S. Belyaev, 3835 Elijah Ct., #528, San Diego, CA (US) 92130

( * ) Notice: Subject to any disclaimer, the term of this patent is extended or adjusted under 35 U.S.C. 154(b) by 0 days.

(21) Appl. No.: 10/898,717

(22) Filed: Jul. 23, 2004

Related U.S. Application Data

(60) Provisional application No. 60/490,350, filed on Jul. 24, 2003.

(51) Int. Cl.
C12N 15/09 (2006.01)
C12N 15/00 (2006.01)
C07K 14/00 (2006.01)
C07K 1/00 (2006.01)

(52) U.S. Cl. ............... 435/320.1; 435/69.1; 530/350; 530/300

(58) Field of Classification Search ............ 435/320.1, 435/69.1; 530/350, 300
See application file for complete search history.

(56) References Cited

U.S. PATENT DOCUMENTS 5,521,084 A * 5/1996 Kowalski et al. ............ 435/325
6,448,377 B1 * 9/2002 Kobilka et al. ............. 530/350
6,461,863 B1 * 10/2002 Jarvis ...................... 435/320.1

FOREIGN PATENT DOCUMENTS

JP 08308564 A 11/1996
WO WO 9806835 A2 * 2/1998

OTHER PUBLICATIONS

Caspers et al., "Overproduction of bacterial chaperones improves the solubility of recombinant protein tyrosine kinases in *Escherichia coli*," Cell Mol Biol 40(5):635-644, 1994.*
Ernst et al., "Direct cloning into the *Autographa californica* nuclear polyhedrosis virus for generation of recombinant baculoviruses," Nucl Acids Res 222(14):1994.*
Gurney et al., "Genomic structure, chromosomal location and conserved alternative splice forms of thrombopoietin," Blood 85(4):981-988, 1995.*
Merrihew et al., "Chromosomal integration of transduced recombinant baculovirus DNA in mammalian cells," J Virol 75(2): 903-909, 2001.*
Amrein et al., "Purification and Characterization of Recombinant Human p50$^{csk}$ Protein-Tyrosine Kinase from an *Escherichia coli* Expression System Overproducing the Bacterial Chaperones GroES and GroEL", Proc. Natl. Acad. Sci., 92:1048-1052, Feb. 1995.
Ashiuchi et al., "In Vivo Effect of GroESL on the Folding of Glutamate Racemase of *Escherichia coli*", J. Biochem., 117:495-498, 1995.

(Continued)

Primary Examiner—Jon Weber
Assistant Examiner—Rosanne Kosson
(74) Attorney, Agent, or Firm—DLA Piper US LLP

(57) ABSTRACT

A recombinant genome comprising polynucleotides encoding at least two additional molecular chaperones and a protein of interest, recombinant baculovirus vectors providing molecular chaperones and a method for producing a foreign protein using said genomes and vectors.

20 Claims, 12 Drawing Sheets

OTHER PUBLICATIONS

Ailor et al., "Overexpression of a Cytosolic Chaperone to Improve Solubility and Secretion of a Recombinant IgG Protein in Insect Cells", *M. J. Biotechnol. Bioeng.*, 58:196-203, 1998.

Blum et al., "Dnak-Mediated Alterations in Human Growth Hormone Protein Inclusion Bodies", *Biotechnology*, 10:301-304, Mar. 1992.

Caspers et al., "Overproduction of Bacterial Chaperones Improves the Solubility of Recombinant Protein Tyrosine Kinases in *Escherichia coli*", *Cellular and Molecular Biology*, 40(5):635-644, 1994.

Cunnea et al., "ERdj5, an Endoplasmic Reticulum (ER)-resident Protein Containing DnaJ and Thioredoxin Domains, Is Expressed in Secretory Cells or Following ER Stress", *Journal of Biological Chemistry*, 278(2):1059-1066, Jan. 2003.

Dale et al., "Increased Solubility of Trimethoprim-Resistant Type S1 DHFR from *Staphylococcus aureus* in *Escherichia coli* Cells Overproducing the Chaperonins GroEl and GroEs", *Protein Engineering*, 7(7):925-931, 1994.

Glover et al., "Hsp104, Hsp70, and Hsp40: A Novel Chaperone System that Rescues Previously Aggregated Proteins", *Cell*, 94:73-82, Jul. 10, 1998.

Higgins et al., "Clanexin Co-Expression and the Use of Weaker Promoters Increase the Expression of Correctly Assembled Shaker Potassium Channel in Insect Cells", *Biochimica et Biophysica Acta*, 1610:124-132, 2003.

Hu et al., "In Vitro Reconstitution of Functional Hepadnavirus Reverse Transcriptase with Cellular Chaperone Proteins", *Journal of Virology*, 76(1):269-279, Jan. 2002.

Hsu et al., "Coexpression of Molecular Chaperone BiP Improves Immunoglobulin Solubility and IgG Secretion from Trichoplusia Ni Insect Cells", *Biotechnology Prog.*, 13:96-104, 1997.

Hsu et al., "Rescue of Immunoglobulins from Insolubility Is Facilitated by PDI in the Baculovirus Expression System", *Protein Expression and Purification*, 7:281-288, 1996.

Hsu et al., "Effects of Co-Expressing Chaperone BiP on Functional Antibody Production in the Baculovirus System", *Protein Expression and Purification*, 5:595-603, 1994.

Lauvau et al., "Tapasin Enhances Assembly of Transporters Associated with Antigen Processing-Dependent and -Independent Peptides with HLA-A2 and HLA-B27 Expressed in Insect Cells", *The Journal of Biological Chemistry*, 274(44):31349-31358, Oct. 29, 1999.

Miyasaka et al., "Characterization of Human Taurine Transporter Expressed in Insect Cells Using a Recombinant Baculovirus", *Protein Expression and Purification*, 23:389-397, 2001.

Naylor et al., "Contribution of Molecular Chaperones to Protein Folding in the Cytoplasm of Prokaryotic and Eukaryotic Cells", *Biochem. Soc. Symp.*, 68:45-68, 2001.

Perez-Perez et al., "DNAK/DNAJ Supplementation Improves the Periplasmic Production of Human Granulocyte-Colony Stimulating Factor in *Escherichia coli*", *Biochem. Biophys. Res. Comm.*, 210:524-529, 1995.

Schrag et al., "Lectin Control of Protein Folding and Sorting in the Secretory Pathway", *Trends in Biochemical Sciences*, 28(1):49-56, Jan. 2003.

Shen et al., "Identification and Characterization of a Novel Endoplasmic Reticulum (ER) DnaJ Homologue, Which Stimulates ATPase Activity of BiP in Vitro and Is Induced by ER Stress", *The Journal of Biological Chemistry*, 277(18):15947-15956, 2002.

Shusta et al., "Increasing the Secretory Capacity of *Saccharomyces cerevisiae* for Production of Single-Chain Antibody Fragments", *Nature Biotechnology*, 16:773-777, Aug. 1998.

Stieger et al., "The Production of Soluble Recombinant Proteins in *E. coli* Assisted by Molecular Chaperones", *Immunology Methods Manual*, pp. 39-44, 1997.

Suzuki et al., "Efficient Protein Production Using a Bombyx Mori Nuclear Polyhedrosis Virus Lacking the Cysteine Proteinase Gene", *Journal of General Virology*, 78:3073-3080, 1997.

Szabo et al., "The ATP Hydrolisis-Dependent Reaction Cycle of the *Escherichia coli* Hsp70 System-DnaK, DnaJ, and GrpE", *Proc. Natl. Acad. Sci.*, 91:10345-10349, Oct. 1994.

Tate et al., "Molecular Chaperones Stimulate the Functional Expression of the Cocaine-sensitive Serotonin Transporter", *The Journal of Biological Chemistry*, 274(25):17551-17558, Jun. 18, 1999.

Tsujita et al., "Apolipoprotein-Mediated Cellular Cholesterol/Phospholipid Efflux and Plasma High Density Lipoprotein Level in Mice", *Biochemica et Biophysica Acta*, 1485:199-213, 2000.

\* cited by examiner

CHAPERONE EXPRESSION GENOMES

RELATED APPLICATIONS

This application claims the benefit of priority to under 35 U.S.C. §119(e)(1) of U.S. Ser. No. 60/490,350, filed Jul. 24, 2003, the entire content of which is incorporated herein by reference.

FIELD OF THE INVENTION

This invention relates in general to a genome expressing additional molecular chaperones simultaneously with a protein of interest in order to assure better folding of a protein of interest.

BACKGROUND OF THE INVENTION

High level expression of proteins, such as for use as biopharmaceuticals, requires proper protein folding for optimal biological activity. Overexpressed proteins are often misfolded and form biologically inactive insoluble protein aggregates, known as inclusion bodies. The formation of inclusion bodies is most often observed in the widely used *E. coli* expression system. In part this is due to inadequacy of prokaryotic cell protein expression machinery, which is unable to provide modifications required for biological activity of many eucaryotic proteins. For example, prokaryotic cells do not have endoplasmic reticulum, with its specific oxidative environment, as well as characteristic set of factors assisting protein folding, as well as protein modification enzymes and protein folding quality control mechanisms. However, inclusion body formation is often a problem in any eucaryotic expression system, if the level of a recombinant protein expression is practically as high as in the *E. coli*, for example in yeast, baculovirus or alpha virus expression systems. The main reason for that is that even though a eucaryotic cell may have an entire set of factors required for a particular protein folding and modification, the concentration of some of these factors is not sufficient to assist the modification and folding of a bulk of recombinant protein produced to an unnaturally high level. Providing factors responsible for protein folding at levels comparable with an amount of an overexpressed protein is required to solve this problem. Such factors are known as molecular chaperones.

We will be using the term molecular chaperone for any factor as far as it can assist protein folding. Ideally, a set of molecular chaperones should be provided, as chaperones act in ensembles. Therefore, a vector system allowing expression of several molecular chaperones at the same time is required for optimal protein folding assistance. In prokaryotes this task is simplified by the fact that several proteins can be expressed from the same promoter comprising an operon. In eucaryotic expression system the task is more complex, as every polynucleotide sequence encoding a protein should be provided with its own promoter or an IRES element (Wilson J. E. et al., Mol Cell Biol., 20:4990–4999, 2000).

Furthermore, in order to achieve maximum expression of a protein of interest, it is desirable to separate polynucleotide sequences encoding a protein of interest from polynucleotide sequences encoding molecular chaperones. Otherwise situated nearby in the genome promoters compete for a local pool of transcription factors. Since the employed promoters are very strong, they can deplete a local pool of transcription factors and ribonucleotide triphosphates, and a transcriptional activity from the nearby promoters, for example one controlling expression of a protein of interest and another controlling expression of a molecular chaperone could be compromised. This is particularly undesirable in respect to a promoter controlling expression of a protein of interest, since majority of the molecular chaperones are expressed to a very high level anyway. Moreover, less production of a molecular chaperone than of a protein of interest is typically required, since chaperones are recyclable and interact with a newly synthesized unfolded pool of a protein of interest, rather than with the entire pool of the protein. Therefore, placing transcriptional units encoding molecular chaperones in vicinity of each other is usually acceptable. However, separating a transcriptional unit encoding a protein of interest from any other strong transcriptional unit is preferred.

Another factor influencing performance of a multi-protein expression system is an ability to provide all the interacting proteins using as few genomes as possible. Preferably, all the polynucleotide sequences encoding for proteins interacting with each other should be provided in a single genome. For example, polynucleotide sequences encoding a protein of interest and key molecular chaperones facilitating its folding should be resident in the same plasmid DNA or in the same recombinant virus DNA, or incorporated into the same host cell genome. Performance of a multi-protein expression system is decreasing with increasing the number of genomes expressing interacting proteins due to several factors.

First, replicating genomes compete for the cell resources and expression of a protein of interest could be reduced to only about ⅓ if 3 genomes, for example 3 recombinant viruses are used at equal multiplicity of infection (m.o.i) to co-infect appropriate host cells, for example to provide for expression of a protein of interest and two molecular chaperones.

Second, due to random Poisson distribution of each type of virus between the cells, different individual cells can receive viruses of each type at different ratios. For example, it is known that for optimal folding of a protein of interest a cell should receive equal amount of each of 3 types of viruses (ratio 1:1:1), one expressing a protein of interest and another two expressing molecular chaperones. To this end, appropriate host cells can be co-infected at equal m.o.i., for example m.o.i. 10 with each type of virus. However, only a minority of cells in the population will receive all 3 viruses at the desired ratio 1:1:1. Some of the cells will receive less virus expressing a protein of interest and more of the viruses expressing molecular chaperones, in these cells expression of protein of interest would be further compromised. In other cells, which did not receive sufficient amount of at least one virus expressing a molecular chaperone, folding of protein of interest could be compromised.

Third, even if some cells received all 3 viruses at a desired ratio, for example 1:1:1, at any time point only a minority of these cells will harbor 3 types of genomes at the same ratio 1:1:1. This is due to the fact that different virus particles are not penetrating the cell simultaneously, and some are starting to replicate before the others. Typically, the process of virus adsorbtion takes about 1 h, and replication of a virus genome can take as little as a minute. Therefore, a number of the genomes of the virus, which infected cell late in adsorbtion process can be dramatically reduced compared to the number of the virus genomes, which entered the cell earlier in the process.

Similarly, different cells can be receiving different number of plasmid genomes and at different times at co-transfections. The co-transfection process differs as it involves a factor of antibiotic selective pressure to eliminate cells, which did not receive a plasmid. However, even under the selection pressure, different cells can have different copy number of the plasmids and can widely vary in the level of correctly processed protein (Keith M. B. et al., Biotechnol. Progr., 1999, 15: 1046–1052). In sum, due to inherent disadvantages of introducing several genomes into the host cells, a multi-protein expression system where all the proteins are obtained from the same genome is much more efficient.

With variable success, supplementing production of a protein of interest with molecular chaperones was widely used for improving protein solubility in the *E. coli* expression system. In this system a protein of interest was provided on a separate plasmid genome from molecular chaperones, which were provided on one or more plasmids.

Obtaining a recombinant protein of interest at a high expression level in a soluble form is the best possible scenario, however this is not always achievable. Sometimes substantial part of the protein is soluble, but the expression level is low. Very often the expression level is high, but the protein is insoluble. Many heterologous proteins are degraded by proteases and fail to achieve high expression levels. Thus, advantages of inclusion body formation is that it protects the expressed protein against degradation by proteases in host cells, can achieve high expression levels and allows separation of the inclusion body by centrifugation from the other proteins. In order to obtain the desired biologically active protein, however, it is necessary for the inclusion body to be denatured and solubilized, followed by renaturation (refolding). This solubilization-renaturation process is performed by repeated trial and error for individual proteins, but often fails to achieve satisfactory recovery rates. In some cases, renaturation is not always possible. Well-established means for solving such problems of insolubilization and degradation of expression products have not been found. Protease mutants of *E. coli* and baculovirus have been produced in order to reduce the degradation of foreign proteins (Suzuki T. et al., J. Gen. Virol., 1997, 78:3073–3080). However, attempts to mass-produce biologically active proteins have not always been altogether successful. In order to solve this problem, co-expression of chaperones and the like has been known. It may result in production of a soluble correctly folded protein, which is less prone to protein degradation, or in inclusion bodies, which may contain largely correctly folded protein.

Most of the studies on protein solubility improvement using molecular chaperones have been performed in *E. coli*. In *E. coli*, DnaK, DnaJ and GrpE chaperones cooperatively act in protein folding. These chaperones belong to Hsp70 molecular chaperone system, which is characteristic for nearly all types of prokaryotic (except some archaebacteria) and all types of eucaryotic cells. It has been considered that the ATP bound to DnaK is first hydrolyzed upon DnaJ binding to an unfolded protein substrate, resulting in the formation of an unfolded protein-DnaJ-DnaK (ADP binding type) complex, and thereafter ADP/ATP exchange takes place by GrpE, resulting in the release of the protein substrate from the complex (Szabo, A. et al., Proc. Natl. Acad. Sci. USA, 1994, 91: 10345–10349).

The DnaK and DnaJ genes are located at the same operon on the *E. coli* chromosome, while the GrpE gene is located at a site apart from the above operon. To date, there have been reported a method of coexpression of a desired protein with DnaK alone or with both DnaK and DnaJ (Blum, P. et al., BioTechnol. 1992, 10: 301–304; Perez—Perez, J. et al., Biochem. Biophys. Res. Comm. 1995, 210: 524–529); a method of coexpression of a desired protein and DnaJ alone (Japanese Patent Laid-Open No. Hei 8-308564); a method of expression of DnaK and DnaJ, and of GrpE from respectively different plasmids (Caspers, P. et al., Cell. Mol. Biol. 1994, 40: 635–644); and a method of independent expression of DnaK and DnaJ and of GrpE from the same plasmid using the same promoter (Stieger, M. and Caspers, P., 1997, Immunology Methods Manual: 39–44). However, these methods have the drawbacks described below.

Specifically, DnaK, DnaJ and GrpE, which act in cooperation with each other, are expected to be more effective when coexpressed, and it is very likely that their inherent chaperone function is not fully exhibited simply when DnaK alone or only DnaK and DnaJ are expressed. Also, in a method in which DnaK and DnaJ, and GrpE, are expressed from the respectively different plasmids, since it is difficult for a total of three plasmids, including the expression plasmid for the desired protein, to coexist in *E. coli*, the gene for GrpE and the gene for the desired protein are placed on a single plasmid, which in turn necessitates that the expression plasmids be constructed to adapt to individual desired proteins. Moreover, since the same promoter is used for expression of GrpE and the desired protein, the expression of the desired proteins cannot be increased to sufficient levels. Further, in the method in which DnaK, DnaJ, and GrpE are independently expressed from the same plasmid using the same promoter, another problem that arises is plasmid stability because of the presence of two units of the same promoter.

There have been reported a number of successful cases of solubilization of foreign proteins that otherwise remain insolubilized in *E. coli* by coexpression of the foreign protein and GroEL and GroES. Examples thereof include, for instance, tyrosine kinase (Caspers, P. et al., Cell Mol. Biol. 1994, 40: 635–644; Amrein, K. E. et al., Proc. Natl. Acad. Sci. USA 1995, 92: 1048–1052); glutamate racemase (Ashiuchi, M. et al., J. Blochem. 1995, 117: 495–498); and dihydrofolate reductase (Dale, G. E. et al., Protein Eng. 1994, 7: 925–931). Other reported cases include improvement of solubility of human growth hormone by coexpression of DnaK (Blum, P. et al., Biotechnol. 1992, 10: 301–304), transglutaminase solubilization by coexpression of DnaJ (Japanese Patent Laid-Open No. Hei 8-308564), and tyro sine kinase solubilization by coexpression of DnaK, DnaJ and GrpE (Caspers, P. et al., 1994, Cell Mol. Biol. 40, 635–644).

A majority of studies on constructing expression systems supplementing protein expression with molecular chaperones pertains to *E. coli* vectors. However, improved performance of eucaryotic expression systems by supplementing them with molecular chaperones has been reported.

Like in bacteria, in eucaryotic cells, the role of molecular chaperones in protein folding is well documented (Naylor D. J. and Hartl F. U., Biochem. Soc. Symp., 68: 45–68, 2001). Ubiquitous Hsp70 chaperone systems play a pivotal role in folding a large variety of proteins in multiple compartments of eucaryotic cells. The Hsp70 system is composed of Hsp70 (DnaK-like) and Hsp40 (DnaJ-like) chaperones. Like in *E. coli*, interaction with DnaJ homologues is essential for full activity of Hsp70. Characterized by the presence of a highly conserved 70-amino acid J domain, Dna-J homologues activate the ATPase activity of Hsp70 proteins and stabilize their interaction with unfolded substrates. There are heat-induced (Hsp70) and constitutively expressed (Hsc70) chaperones. Numerous studies have shown that DnaJ-like proteins can target substrates to Hsp70 or recruit Hsp70 proteins to substrates. In each eucaryotic cell there are a large number of Hsp70 and Hsp40 homologues, at least some of which are believed to have one or more preferred partners. For example, in the cytoplasm Hsc70 preferably interacts with constitutively expressed Hsp40 homologue dj2 (Shen et al., J. Biol. Chem., 277: 15947–15956, 2002), however, Hsp70 endoplasmic reticulum homolog Bip is likely to interact with Hsp40 homologs resident in the endoplasmic reticulum, for example HEDJ (ERdj3), ERdj4 and ERdj5 (Shen Y. et al., J. Biol. Chem., 277: 15947–15956, 2002; Cunnea P. M et al., J. Biol. Chem., 278: 1059–1066, 2003). In addition to the ubiquitous Hsp70 system, there are many other chaperones interacting with certain subsets of proteins.

For example, PDI and ERp57 participate in folding of proteins containing disulfide bonds, PPI in folding proteins containing prolin residues, Hsp90 is essential for folding steroid receptors. Lectin chaperones calreticulin and calnexin act in concert with UDP-glycoprotein glycosyl transferase, mannosidase I, glucosidase II and ERp57 to achieve quality control of glycoprotein folding in the endoplasmic reticulum (Schrag J. D. et al., Trends in Biochemical Sciences, 28: 49–57, 2003).

Hsp70 chaperone system can facilitate folding of a large variety of proteins, however for some proteins additional chaperones are required to extend protein folding capacity of the basic Hsp70 system. Hsp90 chaperone can be recruited to Hsp70 via Hop, which can bind simultaneously to both chaperones, thus facilitating their cooperative action. For example, Hsp70, Ydj1 (yeast homolog of Hsp40), Hsp90 and Hop were required for in vitro folding of functional hepadnavirus reverse transcriptase, and the fifth protein, p23, further enhanced the process. None the proteins alone, nor only two proteins in combination facilitated the protein folding except a combination of Hsp70 and Ydj1, which showed only a weak activity (Hu, S. et al. J. Virol., 76: 269–279, 2002). However, it has to be noted that a combination of human Hsp70 and yeast Ydj1 is unlikely to be optimal, as they come from distant organisms. It is known that Hsp70-like chaperones have preferred Hsp40-like chaperones partners even when they are derived from the same organisms, therefore the activity of the basic Hsp70 chaperone system could be underestimated in this experiment.

In addition to Hsp70 chaperone system, many other chaperones can contribute to protein folding, for example proteins regulating activity of Hsp70 chaperone system, comprising proteins belonging to groups of Hip and BAG-1; chaperonins and co-chaperonins comprising Hsp60, Hsp10, CCT, prefoldin (GimC); small Hsps, comprising Hsp24, Hsp25, Hsp27, Hsp28; PPIases (immunophilins); eucaryotic trigger factor homologues of nascent polypeptide-associated complex such as alpha and beta NAC. Of particular interest to obtaining soluble overexpressed proteins is the Hsp100 group of molecular chaperones, for example yeast Hsp104 or plant Hsp101 which are similar to E. coli CLPs. Hsp100s do not prevent protein aggregation of misfolded protein, however in concert with Hsp40 and Hsp70, Hsp104 can reactivate proteins that have been allowed to aggregate. Hsp104 can not cooperate with E. coli DnaK system, however it is compatible with mammalian Hsp70 system (Glover, J. R. and Lindquist, S., Cell, 94: 73–82, 1998).

There are several reports on improving protein folding and activity using molecular chaperones in higher eucaryotic expression systems. However, no convenient vector system, allowing delivery of a chaperone in the same genome with a protein of interest has been developed.

In yeast, overexpression of Bip and/or PDI has been demonstrated to facilitate secretion of single-chain antibody fragments (Shusta, E. V., et al., Nature Biotechnology, 16: 773–777, 1998). Bip and PDI acted synergistically, though a noticeable effect was also achieved with Bip or PDI alone. First, a gene encoding a protein of interest was stably inserted into the yeast genome, and polynucleotide sequences encoding Bip and PDI were provided on 2 plasmids, which were delivered into cells by co-transfection. Several times improvement was achieved in the production of secreted protein product. However the system is complex. It required the steps of incorporation of a protein of interest into the yeast genome, co-transfection of the plasmids with chaperone, and screening yeast recombinants expressing them at a desirable level. It is unclear if the obtained yeast strain is suitable for a scaled up protein production, as the plasmids were maintained in the episomal state, which is known to have a stability problem, well documented for 2 micron plasmid derivatives, such as was used to express PDI.

Improvement in folding of several proteins of interest was achieved by co-infecting insect cells with recombinant baculoviruses expressing the proteins of interest and recombinant baculoviruses expressing molecular chaperones. Co-expression of Bip or PDI or Hsp70 with IgG improved IgG solubility and secretion (Hsu T. A. et al., Protein Expr. Purif., 5: 595–603, 1994; Hsu T. A. et al., Protein Expr. Purif, 7: 281–288, 1996; Hsu T. A. and Batenbaugh, M. J., Biotechnol. Progr., 13: 96–104, 1997; Ailor E. and Batenbaugh, M. J., Biotechnol. Bioeng., 58: 196–203, 1998). PDI can act as a subunit of microsomal triglyceride transfer protein (MTP). Specialized human chaperone tapasin enhanced assembly of transporters associated with antigen processing-dependent and -independent peptides with HLA-A2 and HLA-B27 expressed in insect cells (Lauvau, G. et al., J. Biol. Chem., 274: 31349–31358, 1999). Co-expression of Hsp70 with Epstein-Barr virus replication protein, BZLF1 slightly improved its solubility, whereas introducing additional chaperones Hsp40 or its homologue Hsdj increased BZLF1 solubility 8 times (Yokoyama N. et al., Biochim. Biophys. Acta, 1493: 119–124, 2000). Co-expression of lectin chaperone calnexin with taurin transporter improved its specific activity by 53% (Miyasaka, T. et al., Protein Expr. Purif., 23: 389–397, 2001). In a separate study, co-expression with calnexin was used to improve expression of correctly assembled Shaker potassium channel in insect cells (Higgins M. K. et al., Biochim. Biophys. Acta, 1610: 124–32, 2003) Co-expression with calnexin, calreticulin, Bip and foldase (ERp57) was employed to improve expression of functional cocaine-sensitive serotonine transporter (Tate C. G. et al., J. Biol. Chem., 274: 17551–17558, 1999). In this study co-expression with calreticulin or Bip or calnexin had a positive effect, which was most pronounced with calnexin, resulting in nearly 3 times improvement in the specific activity. In another study, co-expression of calreticulin with lipoprotein lipase resulted in 9-fold increase in its enzymatic activity, however co-expression with calreticulin was less effective (Zhang L. et al., J. Biol. Chem., epub ahead of print, May 9, 2003). It appears that the degree of positive effect in co-expression experiments with particular molecular chaperones largely depends on the nature of a protein of interest. In most of these papers a positive effect on the folding of proteins of interest was noted, however typically a majority of overexpressed protein of interest remained insoluble. This could be due to a) often providing only one, or at best two molecular chaperones, and b) inherent disadvantages of co-infection method employed in these studies.

Studies on employing molecular chaperones for improved folding of proteins of interest in mammalian cells are few and suffer from the same drawbacks. No improvement in recombinant protein secretion was observed when Bip or PDI were overexpressed in mammalian cells (Dorner A. J. and Kaufman, R. J., Biologicals, 22: 103–112, 1994; Davis, R., Biotechnol. Progr., 16: 736–743, 2000). This differs from the discussed above data on the positive effects of overexpression of PDI in yeast cells or in insect cells co-infected with recombinant baculoviruses. However, different recombinant proteins and host cells were used in these studies, so the data cannot be directly compared. It is possible that level of PDI or Bip activity may not necessarily be a factor limiting recombinant protein folding in the mammalian cells used in these studies. Interestingly, overexpression of PDI can increase longevity of both mammalian cells (Kitchin, K and Flickinger, M. C., Biotechnol. Progr., 11: 565–574, 1995) and insect cells infected with recombinant baculoviruses.

Human Hsp40, or Yeast Hsp 104 or *E. coli* GroEL reduced protein aggregate formation and cell death caused by accumulation of intracellular inclusions in COS-7 cells (Bao Y. P. et al., J. Biol. Chem., 277: 12263–12269, 2002). The aggregates were intranuclear poly-A binding protein with an expanded polyalanine stretch, which is used as a model system of oculopharyngeal muscular dystrophy. These chaperones also reduced aggregation of green fluorescent protein provided with long polyalanine stretches.

To summarize, overexpression of molecular chaperones can improve protein folding and significantly increase yield of biologically active protein of interest. This was demonstrated in numerous studies performed in bacterial, yeast, insect and mammalian cells. Chances that the majority of an overexpressed cytoplasmic protein of interest could be produced in a biologically inactive form of inclusion bodies could be as high as about 50% and are likely to be more than 50% if a protein requires processing in the endoplasmic reticulum. Apparently, this justifies routine use the protein expression systems supplemented with molecular chaperones. Why would anybody use a system without molecular chaperones, if the system with molecular chaperones were working just as well in every respect, and in addition were likely to increase yield of a biologically active proteins? The explanation is that systems supplemented with chaperones are cumbersome and unreliable, and therefore they are very rarely used. For the same reason few such systems are commercially available. Therefore, typically, fast and convenient vectors without the chaperones are used, with the hope that the protein of interest will be soluble. If it is not, a time consuming trial and error approach for denaturing and refolding insoluble protein is applied. If that does not work, many researchers are likely to modify the protein sequence and start the protein expression work from the scratch or drop the protein, rather than apply molecular chaperones, as the chaperones systems are either not available or cumbersome or require additional expertise.

Insect cells are of growing importance for the production of recombinant proteins. A convenient and versatile baculovirus vector system using insect cells has been developed. Although information on the physiology of insect cells is rather scarce, vaccines produced via baculovirus recombinant techniques are generally well accepted. Recombinant immunodeficiency virus type I, parvovirus B19 and H5 influenza vaccines based on baculovirus-expressed proteins have been tested in clinical trials (Treanor J. J. et al., Vaccine, 19: 1732–1737, 2001).

Scale-up suspension cultures offer the best possibility for mass protein production. In large-scale production (see Tramper et al., Rec. Adv. Biotech., 1992, 263–284; Power and Nielsen, Cytotechnology 20: 209–219, 1996), special emphasis should be given to factors influencing cell growth and virus production. Variations in such factors greatly influence the final level of recombinant protein production.

Baculoviruses are characterized by rod-shaped virus particles which are generally occluded in occlusion bodies (also called polyhedra). The family Baculoviridae can be divided in two subfamilies: the Eubaculovirinae comprising two genera of occluded viruses—nuclear polyhedrosis virus (NPV) and granulosis virus (GV)—and the subfamily Nudobaculovirinae comprising the nonoccluded viruses. The cell and molecular biology of *Autographa californica* (Ac)NPV has been studied more in detail.

Many proteins have been expressed in insect cells infected with a recombinant baculovirus encoding that protein. Encoding means that such viruses are provided with a nucleic acid sequence encoding a heterologous protein and often are further provided with regulating nucleic acid sequences, such as a promoter. Most often, the polyhedrin promoter is used to express a foreign gene but the p10 promoter is equally well suited and used as well.

Several cell-lines are available for infection with recombinant baculovirus. The cell-line SF-21 was derived from ovarial tissue of the fall armyworm (*Spodoptera frugiperda*). A clonal isolate, SF-9, available from the American Type Culture Collection (CRL 1711), is more or less a standard cell-line for in vitro production of recombinant virus and is said to be superior in producing recombinant virus. Other cell-lines are, for example, the Hi-Five cell-line and the Tn-368 and Tn-368A cell-lines obtained from the cabbage looper (*Trichoplusia ni*). The most widely used media in which insect cells grow include TC-100, TNM-FH, BML-TC/10, and IPL-41. These media are usually supplemented with more or less defined components, such as mammalian sera, in particular, fetal calf serum. Serum replacements have also been applied to insect-cell culture, and serum-free media, such as Ex-cell 400 and Sf900 are commercially available.

Insect cells, in general, grow on solid supports as well as in suspension, but are reported to give higher yields of virus when grown on solid supports. Infection is most efficient when cells are infected in the exponential growth phase. The amount of polyhedra and virus produced per cell, however, does not vary significantly between cells infected during different stages in the cell cycle. Cell density has a great influence on virus production. Insect cells can show a form of contact inhibition resulting in reduced virus production at higher cell densities.

The initial multiplicity of infection ("m.o.i." or "MOI"), which is the number of infectious viruses per cell, generally influences both the fraction of infected cells and the number of polyhedra per cell at the end of infection. a study (Licari and Bailey, Biotech. Bioeng., 37:238–246, 1991) of a recombinant baculovirus expressing beta-galactosidase, Sf-9 cells were infected with m.o.i. values between 0 and 100. The beta-galactosidase yield increased and cell density decreased with increasing m.o.i. It is generally thought that increasing or decreasing m.o.i. has only a limited affect on the maximum achievable yield of a recombinant protein per infected cell. Choosing low m.o.i., however, allows reduction of virus stock needed for infection and minimizes the risk of the generation of defective interfering particles of baculovirus. If a batch culture of insect cells is infected at high m.o.i. (>5), the ensuing infection process will be essentially synchronous, i.e., all cells will go through the infection cycle simultaneously.

It is necessary to know the titer of the virus stocks in order to be able to plan experiments with desired m.o.i. Methods for determining titer of the virus stocks are well developed and kits designed to simplify this essential procedure are marketed by several companies.

Through designing mathematical models, it is thought possible to predict complex behaviors such as those observed when infecting cells at low m.o.i. or when propagating virus in a continuous culture system. A purely empirical analysis of the same phenomena is considered very difficult, if not impossible. At present, three models are known: the Licari & Bailey, the de Gooijer and the Power & Nielsen model. These are, despite their complexity and the effort that has gone into developing them, all first generation models, postulating about the behavior of baculoviruses expressing a model recombinant protein (beta-galactosidase) expressed under control of the polyhedrin promoter. They summarize, to a large extent, our present quantitative understanding of the interaction between baculovirus and insect cells, when looked upon as a black box system, with disregard to DNA and RNA accumulation and the infection cycle. The binding and initial infection processes are still quantitatively poorly understood and further work in this area is much needed. An expression system involving co-infections with several types of recombinant baculoviruses is even more difficult to describe as it provides another level of complexity.

The present invention provides compositions and methods to improve yield of naturally folded protein of interest by coordinated expression of two or more molecular chaperones with a protein of interest. The invention provides other advantages as well.

SUMMARY OF THE INVENTION

The present invention provides a genome expressing two or more molecular chaperones simultaneously with a protein of interest. In the present invention, the chaperone may be any protein, as long as it is involved in protein folding. More particularly, the present invention relates to a recombinant virus genome, and more particularly to a recombinant baculovirus genome. It is advantageous to be able to express a protein of interest with a comparable amount of several molecular chaperones, as the chaperones act in ensemble in order to assure better folding of a protein of interest. So far, providing several molecular chaperones to improve folding of a protein of interest was achieved by introducing into cells more than one additional genome (FIG. 1A). Typically, chaperones are expressed from one or more plasmid or virus genome, and a protein of interest from a separate plasmid or a virus genome. However, it is difficult, and typically impossible to control the ratio of expression of foreign proteins in individual cells if they are provided on different genomes, for example on different viruses at co-infection, or on different plasmids at co-transfection. Therefore, it is advantageous to express several interacting chaperones in the protein of interest in the same genome (FIG. 1B). Providing the chaperones and a protein of interest in the same genome ensures a certain ratio of their expression in every cell. This certain ratio can be adjusted to a desired level by manipulating regulatory elements controlling transcription of a chaperone gene or/and translation of the mRNA encoding the chaperone. To maintain high level expression of a protein of interest, polynucleotide sequences encoding molecular chaperones are inserted in the genome away from a protein of interest, rather than expressed on separate genomes as it was routinely done so far. Protein of interest can be provided with a powerful signal peptide sequence in order to facilitate it co-translocation with molecular chaperones into the endoplasmic reticulum.

In another embodiment of this invention, we provide a method for producing inclusion bodies consisting of a protein of interest and large amount of molecular chaperones. These inclusion bodies have the same advantages of ease of purification and protection from protein degradation as inclusion bodies produced without large amount of molecular chaperones. However, they contain a protein of interest which is significantly better folded, which manifests in improved recovery of a biologically active protein.

In another embodiment of the invention, there is provided a recombinant baculovirus protein expression system supplemented with molecular chaperones, which is as convenient and reliable as conventional systems. It is based on as a widely used prototype BacPak6 marketed by Clontech (Palo Alto, Calif.), Pharmingen (San Diego, Calif.), Orbigen (San Diego, Calif.). The system of this invention works just as well as the prototype in every respect, i.e. convenience of operation, yield of recombinant clones, protein expression level and strain stability. In addition, it provides sets of molecular chaperones, which we proved to improve protein solubility in the cases of insoluble proteins, which we tested so far. Furthermore, due to expression of a reporter GFP, it allows convenient control of virus propagation and determination of titers of virus stocks. Though the experiments were performed using insect cells-recombinant baculovirus expression system, the invention is of general importance for constructing convenient vectors supplemented with molecular chaperones in bacterial or eucaryotic cells, such as yeast, insect, plant or mammalian cells.

BRIEF DESCRIPTION OF THE DRAWINGS

FIG. 1A shows a scheme providing a gene encoding a protein of interest on one genome and genes encoding molecular chaperones on other genome(s). The gene encoding a protein of interest is separated from the genes encoding molecular chaperones as they are on different genomes.

FIG. 1B shows a scheme providing a gene of interest in the same genome with two or more genes encoding chaperones. The gene encoding a protein of interest is separated from the genes encoding molecular chaperones by a long polynucleotide sequence.

DETAILED DESCRIPTION OF THE INVENTION

Figure 1A:
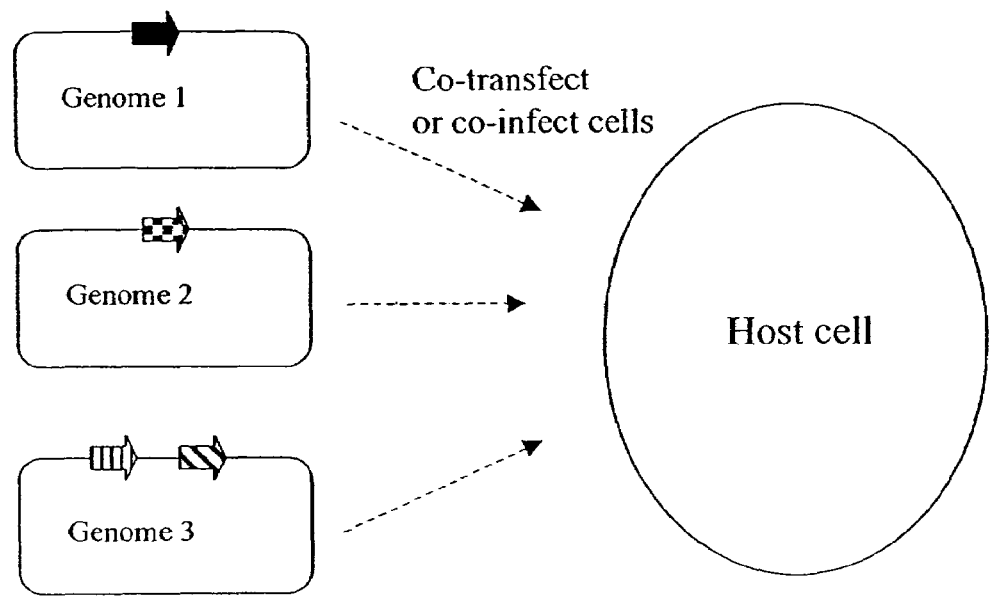
FIGS. 1A and 1B show a comparison of previously disclosed general scheme for expressing a polynucleotide of interest in the presence of multiple polynucleotides expressing molecular chaperones with the invention method.

In the present invention the chaperone may be any protein, as long as it is involved in protein folding. The choice of chaperones for folding a particular protein mainly depends on the intracellular compartmentalization characteristic for a protein or on protein modifications characteristic for a protein, such as disulfide bond formation or glycosylation. Since some proteins are processed in more than one compartment, chaperones operating in more than one compartment may also be employed to facilitate production of certain proteins. For example, cytoplasmic Hsp70 and Hsp40 can be employed for production of proteins, which fold in the endoplasmic reticulum, as they can facilitate protein translocation into the endoplasmic reticulum (Ngosuvan, J. et al., J. Biol. Chem., 278: 7034–7042, 2003). Moreover, chaperones, which are not characteristic to some compartments and to some cells, can be expressed in these cells if their function is desirable for folding proteins expressed in these cells. For example, chaperones belonging to the group of CLPs (bacterial CLP, yeast Hsp104 or plant Hsp101), which can solubilize protein aggregates and recycle misfolded proteins for interaction with molecular chaperones, can be expressed in the cytoplasm of insect or mammalian cells. They can be also expressed in other cell compartments, such as endoplasmic reticulum, mitochondria or nucleus by providing them with specific polypeptide sequences targeting them to these compartments, known to those skilled in the art. For example, yeast Hsp104 can be provided with a hydrophobic translocation signal sequence, for example, a honeybee melittin signal sequence in order to target this chaperone into the endoplasmic reticulum.

Chaperones resident in the cytoplasm are used for folding cytoplasmic proteins. One can use combinations of chaperones acting cooperatively in ensembles. For example, one can use Hsp70 chaperones with Hsp40 chaperones as well as Hsp70 and Hsp40 coming from the same organism in particular. Also, one can use natural Hsp70 and Hsp40 partners, for example human Hsc70 and human dj2, and also use them in combination with additional natural chaperone partners, in particular Hop and Hsp90, which could be also supplemented with p23. Specialized chaperones are known to those skilled in the art (Lauvau G. et al., J. Biol. Chem., 274: 31349–31358, 1999). Typically, chaperones derived from a particular organism can assist folding of proteins derived from another, even evolutionarily distant organism. One can also use chaperones to assist folding of proteins coming from evolutionarily close organisms or from the same organism. More than one chaperone homologue can be used.

There are many chaperones and multiple homologues known to those skilled in the art, which can be used for folding proteins in the cytoplasm. Examples of such chaperones include, for instance Hsp90 chaperones, comprising HtpG(C62.5), fungi Hsp82, Hsc82, Hsp82, mammalian Hsp86 (Hsp90α), Hsp84 (Hsp90β); a group of Hop (Hsc70/Hsp90 organizing protein or p60, Sti1, RF-Hsp70), a group of Hip (Hsc70 interacting protein or p48), a group of BAG-1 (Hap, Hap46, RAP46) a group of p23, a group of Hsp100 (Clps), comprising prokaryotic class I Clps (Clp A, B, C, D, L), pocaryotic class II Clps (Clp M, N, X, Y) and eucaryoticSKD3, Hsp101, Hsp104 (ClpB homologue), a group of Hsp70, comprising prokaryotic DnaK, Hsc66 (HscA), Hsc62 and eucaryotic Hsp72, Hsp73, Hsc70, Prp73, a group of Hsp110 (similar to Hsp70) comprising Apg-1 (Osp94), Apg-2(Hsp70 RY), a group of Hsp40 (DnaJ) comprising prokaryotic DnaJ, CbpA, Hsc20 (HscB), and eucaryotic, Hdj1 (Hsp40), Hdj2 (HSDJ), Hsj1 a/b neurone specific, HLJ1, Ydj1p (Mas5p), Dj1p, Caj1, cysteine-string protein ALA-D, a group I chaperonins comprising prokaryotic GroEL and eucaryotic Cpn60 (Hsp60), group I co-chaperonins comprising prokaryotic GroES and eucaryotic EPF, Cpn10, Hsp10, group II chaperonins comprising prokaryotic TF55 and eucaryotic TriC (CCT), group II co-chaperonins comprising prokaryotic GimC and eucaryotic GimC (Prefoldin), group of small Hsp (sHsps) comprising prokaryotic 1bpA (14 kDa), 1bpB (16 kDa) and eucaryotic Hsp12, Hsp24, Hsp25, Hsp26, Hsp27, Hsp28, Hsp30, a group of GrpE comprising prokaryotic GrpE, a group of immunophilins (PPlases) comprising prokaryotic 10.1 kDa, PPI, CyP18, CyP21, WHP, FKBP33 and eucaryotic CYP1, CYP2, FKBI (RBPI), CyP40, CyPA, FKBP12, FKBP52, group of NAC and TF (trigger factor), comprising prokaryotic TF and eucaryotic alphaNAC and betaNAC, group of PBF, MSF, Mft52 and SecB comprising prokaryotic SecB and eucaryotic Mft52, MSF, PBF.

There are many chaperones and multiple homologues known to those skilled in the art, which can be used to assist protein folding in the nucleus. Examples of such chaperones include, for instance Hsp90 chaperones comprising Hsp90 and Hsp82, Hsp70 chaperones comprising Hsp72 and Hsp73, Hsp110 chaperones (similar to Hsp70), Hsp40 chaperones comprising Hdj1 (Hsp40), Hdj2, Hdj1 a/b neurone specific, small Hsps comprising Hsp24, Hsp25, Hsp26, Hsp27, Hsp28, a group of Hsp100 (Clps), immunophilins (PPlases) comprising CyP-40, FKBP25 and FKBP52. There are many chaperones and multiple homologues known to those skilled in the art, which can be used to assist protein folding in the mitochondria. Examples of such chaperones include mitochondrial molecular chaperones belonging to the group of Hsp100, such as ClpX, Hsp78, Mcx1p, Hsp90, such as Trap1, Hsp75; group of Hsp70, such as mt-Hsp70, Grp75, Pbp74, Ssc1p, Ssh1p, Ssc2p; group of Hsp40 (Dnaj-like); group I chaperonins (Cpn60, Hsp60); group I co-chaperonings (Cnp10, Hsp10); group II chaperonins; group II co-chaperonins; small Hsps; group of GrpE; group of immunophilins (CYP3, CyPD) for folding proteins of interest belonging to mitochondria.

Though the majority of the proteins fold in the cytoplasm, about 25% of animal cell proteins are translocated into the endoplasmic reticulum and are folded there. These proteins can be recognized by the presence of characteristic hydrophobic translocation signal sequence on their amino terminus. Such proteins comprise secreted proteins (interleukins, antibodies), transmembrane proteins (receptors and membrane proteins participating in cell-to cell and inside the cell signaling pathways), and proteins resident in the Golgi and endoplasmic reticulum compartments. Many of these proteins have applications as protein therapeutics or drug targets. Very important viral proteins also belong to this group, for example proteins anchored in the virus lipid outer envelope. These include E1 and E2 proteins of the hepatitis C virus, HbsAg of the hepatitis B virus, gp120 and gp160 of the human immunodeficiency virus, E proteins of West Nile virus, Dengue viruses and Japanese encephalitis virus. Virus envelope proteins contain virus-neutralizing epitopes, and are used for development of vaccines.

Proteins translocated into the endoplasmic reticulum are difficult and sometimes impossible (for example HBsAg of the hepatitis B virus) to produce in biologically active form in prokaryotic expression systems. A method for production of such protein in $E.$ $coli$ by co-expressing said proteins with molecular chaperones and providing them with a prokaryotic signal sequence to facilitate their translocation into the periplasm or medium was described (Dorothee, A., U.S. Pat. No. 6,455,279, 2002). However, prokaryotic cells lack the endoplasmic reticulum compartment with its characteristic oxidizing environment and a set of specific chaperones required for folding these proteins. Therefore production of such proteins in eucaryotic, rather than prokaryotic systems, supplemented with molecular chaperones can provide a higher yield of active protein.

A higher eucaryotic baculovirus system is often a system of choice for production of both cytoplasmic and translocated proteins intended for human vaccines, for example against malaria (Perera, K. L. R. et al., Infect. Immunol., 66:1500–1506, 1998; Hong Liang, D. et al., Infect. Immun., 68: 3564–3568, 2000; Chang H. et al., U.S. Pat. No. 6,420, 523, 2002), dengue viruses (Lai C. J. et al., U.S. Pat. No. 6,184,024, 2001; Kelly S. et al, U.S. Pat. No. 6,514,501, 2003), influenza viruses (Smith G. E., et al., U.S. Pat. No. 5,858,368, 1999; Smith G. E., et al., U.S. Pat. No. 6,245,532, 2001), hepatitis E (Fuerst, T. R. et al., U.S. Pat. No. 6,291,641, 2001), Japanese encephalitis (Lai C. J. et al., U.S. Pat. No. 6,184,024, 2001), rotavirus (Estes M. K., U.S. Pat. No. 5,891,676, 1999) incorporated herein by reference. Baculovirus-expressed proteins can be also utilized for making diagnostics (Jackwood, D. J. et al., U.S. Pat. No. 5,605,827, 1997; Plana D. et al., U.S. Pat. No. 5,888,513, 1999; Pellett, P. E., et al., U.S. Pat. No. 6,126,944, 2000), incorporated herein by reference. There are also examples for development of baculovirus-expressed proteins for therapeutic use, in particular cancer treatment (Fidler I. J. et al., U.S. Pat. No. 6,342,216; 2002; Yamamoto N. et al., U.S. Pat. No. 6,410,269, 2002), incorporated herein by reference. Many proteins intended for vaccine, diagnostic or therapeutic use can be improved by co-expressing them with molecular chaperones using vectors of this invention as typically they provide better folding of the expressed protein.

Another aspect of this invention relates to the improved process of protein translocation into the endoplasmic reticulum combined with improved protein folding. Enhanced secretion from insect cells of a foreign protein fused to an insect signal signal peptide was described (Tessier D. C. et al., Gene 98: 177–183, 1991), however this did not include co-expression with molecular chaperones. In this invention, co-expression of molecular chaperones is combined with improved translocation of a foreign protein into the endoplasmic reticulum using insect signal sequences. Along with the honeybee melittin signal sequence (Tessier D. C. et al., Gene 98: 177–183, 1991), incorporated herein by reference, a range of potent insect signal sequences with different hydrophobicity parameters is provided. Such signal sequences are selected from the group of signal sequences providing massive and fast translocation of a protein through the membrane of the endoplasmic reticulum. Such signal sequences can be from the group of silk proteins, for example $Antheraea$ $mylitta$ fibroin heavy chain, Acc# AY136274 or poison proteins, for example Pimpla hypochondriaca cystein-rich venom protein 6, Acc#AJ438997. These signal sequences are not limited to insect proteins, but can include other massively secreted proteins, for example spider poison or silk proteins or snake poison proteins. Using a selection of signal sequences allows optimization of the protein production parameters, for example protein yield and secretion. Moreover, folding and modification of a translocated protein, for example glycosylation pattern and therefore biological activity and stability can depend on the nature of the signal sequence.

Chaperones, which are used with the proteins translocated into the endoplasmic reticulum include Hsp70 endoplasmic reticulum homologues such as Bip; Dnaj-like chaperones ERdj1, ERdj2, ERdj3, ERdj4, ERdj5; chaperones containing thyreodoxin-like domains and participating in formation of disulfide bonds, such as ERp57 and PDI; Hsp70 similar Grp170 and residing in the ER membrane Stch; Hsp90 homologues residing in the ER, such as Grp94 (ERp90, gp96, endoplasmin); immunophilins (PPlases); Ero1 and Ero2 proteins which can be co-expressed with PDI to manipulate its activity.

For glycoproteins, lectin chaperones, such as calnexin, calreticulin, and mannose specific lectins ERGIC-53, ERGL, VIP36 and VIPL, Hsp70 endoplasmic reticulum homologues including Bip; Dnaj-like chaperones ERdj1, ERdj2, ERdj3, ERdj4, ERdj5; chaperones containing thyreodoxin-like domains and participating in formation of disulfide bonds, such as ERp57 and PDI, proteins regulating activity of PDI, such as Ero1 and Ero2; Hsp70 similar Grp170 and residing in the ER membrane Stch; Hsp90 homologues residing in the ER, such as Grp94 (ERp90, gp96, endoplasmin); immunophilins (PPlases); group of UDP-glucose glycoprotein glycosyl transferase, group of glucosydases, group of mannosidases, can be used to facilitate folding of a glycoprotein of interest.

The present invention provides a recombinant genome encoding the chaperone. The term "recombinant genome" is defined in this invention as any genome, which in addition to naturally present polynucleotide sequences required for its replication contains genes encoding the above-described chaperone, and a polynucleotide sequence either encoding a protein(s) of interest or allowing convenient insertion of a polynucleotide sequence encoding such. In order to achieve high level of expression of molecular chaperones practically without lowering the expression level of a desired protein, it is advantageous to separate a transcriptional unit controlling expression of desired proteins from transcriptional units controlling expression of molecular chaperones. To this end, plasmid transfer vectors can be designed by those skilled in the art to facilitate insertion of polynucleotide sequences of interest into non-essential parts of the baculovirus genome. In concrete example, EGT insertion plasmid transfer vector was designed, which enabled insertion of polynucleotide sequences encoding 3 proteins of interest, including 2 molecular chaperones and a reporter protein into the baculovirus genome.

In one embodiment of the present invention a recombinant genome derived from a baculovirus comprising polynucleotides encoding a polynucleotide sequence of interest in the polyhedrin site and human Hsc70 and dj2 inserted at the distance at least 1000 nucleotides from the polyhedrin site is provided.

In another embodiment in the present invention a recombinant genome derived from a baculovirus comprising polynucleotides encoding a polynucleotide sequence of interest in the polyhedrin site and human Bip and PDI inserted at the distance at least 1000 nucleotides from the polyhedrin site is provided.

In still another embodiment in the present invention a recombinant genome derived from a baculovirus comprising polynucleotides encoding a polynucleotide sequence of interest in the polyhedrin site and human calreticulin and PDI inserted at the distance at least 1000 nucleotides from the polyhedrin site is provided.

The level of expression of molecular chaperones can be adjusted to a desirable level by using stronger or weaker promoters or inducible promoters. As demonstrated in a concrete example, strong promoter can be mutated to produce a weaker promoter, thus moderating the level of expression of an overexpressed chaperone. A ratio of chaperones can be adjusted approximately to the ratio typically observed in the cells, from which said chaperones are derived. Such ratios are known to those skilled in the art (Murphy P., et al., J. Biol. Chem., 276: 30092–30098) or from in vitro protein folding data assisted with molecular chaperones.

As demonstrated in a concrete example, certain restriction endonuclease sites in the polynucleotide sequences encoding molecular chaperones can be mutated. This is useful if selection of recombinant viruses containing a polynucleotide sequence for expressing a protein of interest involves cleavage of a vector DNA with that restriction endonuclease. For example, rescue of baculovirus vector DNA linearized with a restriction endonuclease with a plasmid transfer vector (Kitts P. et al., Biotechniques, 14: 810–817, 1993). In concrete examples described below, Bsu36.I restriction endonuclease sites were mutated in polynucleotide sequences encoding human Hsc70 and human caltreticulin. This allowed highly efficient selection of recombinant baculoviruses, just as efficient as with the prototype BacPak6 vector DNA linearized with Bsu36.I inside and in vicinity of the E. coli beta-galactosidize gene residing in the polyhedrin site. However, as occasion demands, the expression vector may contain any selection marker or a restriction endonuclease site to allow employment of any method for selection of recombinant genomes expressing a protein of interest, for example Bac-to-Bac, Bac-N-Blue, BaculoDirect vector DNA available from Invitrogen, Carlsbad, Calif.

In the invention, the foreign protein or a protein of interest can be any protein as far as it is expressed in more soluble and/or more stable form using said vectors. While not limiting the choice of the protein, such foreign protein can be glycoproteins, disulfide bridges-containing proteins, interferons, interleukins, interleukin receptors, interleukin receptor antagonists, granulocyte colony-stimulating factors, granulocyte macrophage colony-stimulating factors, macrophage colony-stimulating factors, erythropoietin, thrombopoietin, leukemia inhibitors, stem cell growth factors, tumor necrosis factors, growth hormones, proinsulin, insulin-like growth factors, fibroblast growth factors, platelet-derived growth factors, transforming growth factors, hepatocyte growth factors, bone morphogenetic factors, nerve growth factors, ciliary neurotrophic factors, brain-derived neurotrophic factors, glia cell line-derived neurotrophic factors, neurotrophine, prourokinase, tissue plasminogen activators, blood coagulation factors, protein C, glucocerebrosidase, superoxide dismutase, renin, lysozyme, cytochromes including P450s, prochymosin, trypsin inhibitors, elastase inhibitors, lipocortin, reptin, immunoglobulins, single-chain antibodies, complement components, serum albumin, cedar pollen allergens, hypoxia-induced stress proteins, protein kinases, proto-oncogene products, transcription factors, virus structural and non-structural proteins, plant, yeast or bacterial enzymes effecting metabolite modifications.

Protease mutants can be used to stabilize expressed protein. For example, in E. coli cells protease mutants, such as lon mutants, clpPX mutants, plsX mutants, rpoH mutants and combinations of such mutants can be favorably used to more stably express foreign proteins. Insect cell proteases and a protease encoded by baculovirus can be mutated to improve stability of expressed proteins (Bromme D. et al., Biol. Chem. Hoppe Seyler, 1995 376: 611–5).

Many methods known to those skilled in the art can be used to introduce recombinant genomes into the host cells. A calcium chloride method, a rubidium chloride method, an electroporation method, protoplast method and other conventional methods can be used to introduce the said genomes into bacterial cells, such as E. coli.

Transfection methods employing cathionic lipids or liposomes or calcium phosphate precipitation of nucleic acid can be used to deliver genomes into higher eucaryotic cells, for example insect or mammalian cells. Screening for cotransformants can be carried out using chemicals appropriate for selection of marker genes. Recombinant virus genomes can be constructed and most conveniently delivered into the host cells by infecting appropriate cells with recombinant viruses carrying such genomes.

In one embodiment, this invention provides method for constructing recombinant baculovirus genomes using a backbone transfer vector. In this invention, a backbone transfer vector may be any vector as long as it provides insertion of genes of interest into any non-essential site in the baculovirus DNA except polyhedrin. Performance of a backbone insertion vector can be facilitated by constructing a baculovirus DNA, which can be linearized at the insertion site (Yang S. and Miller K., J. Virol. Methods, 76: 51–58, 1998). In this invention, a non-essential site is any site, which can accommodate insertion of additional genes into baculovirus DNA without disrupting virus replication in host cells. A non-essential insertion site, for example a SpeI restriction site in a polynucleotide sequence encoding for Autigrapha californica nuclear polyhedrosis virus EGT protein, is selected. Such sites are known to those skilled in the art. They can be selected within polynucleotide sequences encoding proteins or promoters dispensable for replication in certain host cells or from the intergenic regions of *Autographa californica* nuclear polyhedrosis virus (Acc#NC_001623). A backbone transfer vector can be prepared by amplifying in PCR and inserting the DNA fragment flanking the above site into a suitable cloning vehicle, such as the plasmid pUC19 (Acc#X02514). For example, a backbone transfer vector, designated as a EGT transfer vector, comprises a EGT gene and a suitable cloning vehicle containing determinants for ampicillin resistance and replication in E. coli derived from pUC18 plasmid. The EGT gene is non-essential for baculovirus replication, therefore any site within EGT coding sequence or its promoter can be used for insertion of polynucleotide sequences. Additionally, by appropriate recombinant DNA techniques, the DNA sequences encoding for part or whole of EGT protein or its promoter may be deleted from the above-described transfer vector as far as sufficient flanking regions remain. The size of a flanking sequence can be of about 500–2000 nucleotides or it can be as small as about 50–100 nucleotides and as large as about 10,000 nucleotides.

Potentially any gene(s) or/and transcription control elements(s) can be cloned into the EGT vector, which can be contacted with appropriate baculovirus DNA, so as to effect recombination, thereby incorporating the desired genetic material into the EGT site in the baculovirus genome. Recombination can be accomplished by transfection (Smith G. E. and Summers, M. D., U.S. Pat. No. 4,879,236, 1987). Since this process does not occur in 100 percent of the viruses, the result will be a mixture of nonrecombinant and recombinant viruses.

The recombinant viruses can be selected by hybridizing with a polynucleotide probe selected from the polynucleotide sequence of an insert, for example using dot-blot hybridization method, or by detecting expression of a protein product derived from a gene encoded in the inserted polynucleotide sequence, for example on SDS-PAGE gels or by the reactivity of the protein with antibodies using ELISA or Western blot methods (King L. A. and Possee R. D., The baculovirus expression system. A laboratory guide, Chapman & Hall, London, New York, Tokyo, Melbourne, Madras, 1992).

More conveniently, viruses can be selected by expression of a reporter gene, such as green fluorescent protein or a selectable marker, such as antibiotic resistant gene, for example puromycin resistance gene (Clark R. et al., U.S. Pat. No. 6,428,960, 2002), which can be provided in the EGT vector in a cassette with one or more other genes of interest. This allows for selection of recombinant genomes expressing a protein of interest alongside with one or more genes of interest provided in the cassette. An example of such a cassette is provided below.

Reporter proteins, such as GFP are preferred as they provide means to follow virus propagation in insects to monitor the dose of pesticide in the field, or in insect cell culture, allowing for a more convenient optimization of virus infection or cultivation conditions. A flow cytometry method was used to this end, which employed immunolabeling of the expressed protein (Deparis, V. et al., Biotechnol. Progr., 19: 624–630, 2003). However, the method of this invention is much more simple and straightforward, as it relies on direct detection of GFP, which is provided as a standard feature in the vectors of this invention. Therefore, no immunolabeling is required for detection of virus propagation and protein synthesis. GFP expression is also convenient for titration of virus stocks in laboratory practice. To this end, insect cells are infected with a control virus expressing GFP with a known titer and an experiment virus with an unknown titer, also expressing GFP, and the intensity of green fluorescence is compared about 48 hours post infection. In another embodiment, titration of virus stocks is performed by comparison of the number of green foci of infected cells under a fluorescence microscope with a control and experiment virus. GFP expression is also convenient for pesticide application of recombinant baculoviruses, since GFP provides a monitoring device for infected insects to prevent overuse and can increase virus retention time as a pesticide in the field due to its increased stability (Chao Y. T., U.S. Pat. No. 5,919,445, 1999; Kang S. K. et al, U.S. Pat. No. 6,338,846, 2002), incorporated herein by reference. Importantly, EGT vectors are more suitable for making insecticides, rather than widely used polyhedrin insertion vectors (Smith G. E. and Summers, M. D., U.S. Pat. No. 4,879,236, 1987), since expression of polyhedrin protein is essential for a baculovirus insecticide. When polyhedrin transfer vectors are used to make insecticides, additional manipulations are required, as polyhedrin has to be provided. However, EGT protein is not essential for the virus propagation in insects and no additional manipulations are required when EGT gene is interrupted. In fact, it is a positive development, as EGT deficient baculoviruses make more potent insecticides due to reduced feeding of insect larvae and growth inhibition (Miller L K et al., U.S. Pat. No. 5,662,897, 1997; Miller et al., U.S. Pat. No. 6,156,309, 2000; Chen X. et al., J. Invertebr. Pathol. 76:140–146, 2000).

Therefore, EGT vectors of this invention provide a unique tool for constructing pesticides. They offer an advantage of simultaneous inactivation of EGT gene, resulting in a faster-killing insect virus, expression of GFP resulting in improved virus stability and its monitoring in the field, and enabling expression of one or more protein(s), for example a toxin or/and RNA molecules, for example anti-sense or dsRNA molecules, harmful to the insects (Guarino, L. U.S. Pat. No. 5,162,222, 1992; Granados, R. R. et al., U.S. Pat. No. 5,475,090, 1995; Krause, M. et al., U.S. Pat. No. 5,925,346, 1995; Levings III et al., U.S. Pat. No. 5,665,349, 1997; Miller L K et al., U.S. Pat. No. 5,662,897, 1997; Iatrou K., U.S. Pat. No. 5,989,541, 1999; Miller et al., U.S. Pat. No. 6,156,309, 2000; Iatrou K. et al., U.S. Pat. No. 6,221,632, 2001; Leisy D. J. et al., U.S. Pat. No. 6,265,376; Liu L. et al., U.S. Pat. No. 6,326,193, 2001), incorporated herein as reference. EGT transfer vectors can be used to modify any appropriate baculovirus genome, which has the same or highly homologous EGT sequence as in the transfer vector. It can be used directly to modify a wild type baculovirus genome, or a recombinant baculovirus genome which was already modified and comprise an improved pesticide.

EGT transfer vectors can be also used to modify any recombinant baculolovirus, which is a producer of a recombinant protein. In this case, in addition to a gene encoding recombinant protein of interest in the polyhedrin or other site, other genes encoding additional proteins of interest can be inserted into the EGT site. Vectors of this invention can be used to express multi-protein complexes for producing multi-protein vaccines or complete enzymatic chains participating in synthesis of compounds of pharmaceutical interest, for example polyketides, such as Erythromycin derivatives. The vectors of this invention can be applied for expression of several genes encoding polyketide synthases forming a particular synthetically active combination (McDaniel R. et al., et al. U.S. Pat. No. 6,524,841, 2003; Ashley G. et al., U.S. Pat. No. 6,509,455, 2003; Ashley G. et al., U.S. Pat. No. 6,503,741, 2003; Reeves C et al., U.S. Pat. No. 6,503,737, 2003; Julien B. et al., U.S. Pat. No. 6,410,301 2002; McDaniel R. et al., U.S. Pat. No. 6,403,775, 2002; Khosla C. et al., U.S. Pat. No. 6,391,594, 2002; Betlach M. C. et al., U.S. Pat. No. 6,262,340, 2001; Betlach M. C. et al., U.S. Pat. No. 6,251,636,200; Ziermann R. et al., 6,177,262, 2001; Wu K., U.S. Pat. No. 6,150,513, 2000; Gustafsson C., et al., U.S. Pat. No. 6,090,601, 2000; Ashley G. et al., U.S. Pat. No. 6,117,659, 2000), incorporated herein by reference. Moreover, they can be employed to improve the level of expression and biological activity of these enzymes via co-expression with molecular chaperones, as compared to the enzymes produced in systems not supplemented with chaperones. Multi-plasmid system was employed to facilitate combinatorial biosynthesis of polyketides (Santi, D. V. et al. U.S. Pat. No. 6,399,789, 2002), incorporated herein by reference. However, co-infection process with recombinant viruses is more reliable and cost-efficient than co-transfection. Furthermore, multiple baculovivrus expression vectors of this invention offer a more powerful approach due to ability of express many proteins of interest using the same genome combined with the versatility of co-infection with several such genomes. For example, at least three genes encoding a protein of interest can be inserted into the EGT site, four in the polyhedrin site (Belyaev A. S. and Roy P. Nucleic Acids Res., 21:1219–1223, 1993), and one or two in the p10 site.

EGT transfer vectors can be also used to modify any recombinant baculovirus vector DNA. Such baculovirus vector DNA are known to those skilled in the art. They comprise BaculoGold (PharminGen), BacPAK6 linearized DNA (Clontech, Pharmingen, Orbigen), Sapphire DNA (Orbigen), Bac-to-Bac, Bac-N-Blue, BaculoDirect vector DNA (Invitrogen, Carlsbad, Calif.). All of these vectors provide very high percentage of recombinants, and the choice of the vector largely depends on the training and personal preference of a researcher. However, all these vectors are essentially the same in respect that they facilitate insertion of a foreign gene of interest into the polyhedrin site, and except Sapphire they do not provide any factors assisting protein folding.

Any of these or other vectors providing for insertion into polyhedrin site, or any other non-EGT site can be modified using EGT transfer vectors without negatively affecting cloning efficiency or the protein expression level. In the examples below I modified BacPak6 baculovirus vector DNA using a EGT transfer vector, in which I provided molecular chaperones to assist protein folding and GFP to monitor the virus propagation. Then, using standard polyhedrin site insertion technique, genes encoding proteins of interest were inserted into the polyhedrin site of the parental BacPak6 vector DNA, or into BacPak6 vector DNA modified at the EGT site. All vectors provided the same high efficiency of recombinants and high level of protein expression. However, the modified vectors expressing molecular chaperones provided for expression of more soluble proteins of interest. Improvement in protein solubility was observed with 5 proteins out of 5 tested. Expressed GFP levels allowed for convenient monitoring of propagation of recombinant viruses in the host cells and titration of their virus stocks.

The following examples, which illustrate various methods and compositions in the invention, are intended to illustrate, but not limit the scope of the invention.

EXAMPLES

Starting Materials and Methods

Tag polymerase, T4 DNA ligase and restriction endonucleases may be obtained from New England Biolabs (Beverly, Mass.).

Synthetic oligonucleotide linkers and primers may be prepared using commercially available automated oligonucleotide synthesizers. Alternatively, custom designed synthetic oligonucleotides may be purchased from commercial suppliers. cDNA synthesis kit and random priming labeling kits may be obtained from MWG Biotech (Charlotte, N.C.) or GIBCO/BRL (Gaithersburg, Md.).

Common manipulations used in accordance with the cloning procedures set forth in the examples are described in T. Maniatis, E. F. Fritsch and J. Sambrook, Molecular Cloning: A Laboratory Manual, Cold Spring Harbor Laboratory, 1982. This reference includes procedures for the following standard methods: cloning procedures with E. coli plasmids, transformation of E. coli cells, plasmid DNA purificaton, phenol extraction of DNA, ethanol precipitation of DNA, agarose gel electrophoresis, purification of DNA fragments from agarose gels, and restriction endonuclease and other DNA-modifying enzyme reactions.

Virus stocks used in the examples are prepared and titrated in Spodoptera frugiperda Sf9 cells with TC-100 medium plus 10% fetal bovine serum (King L. A. and Possee R. D., The baculovirus expression system. A laboratory guide, Chapman & Hall, London, New York, Tokyo, Melbourne, Madras, 1992). Another Spodoptera frugiperda cell line Sf21 (IPLB-Sf 21-AE) and another medium TNM-FH (see, Hink W. F., Nature (London), 226: 466–467, 1970) can be used. The manipulations for generating and cultivating recombinant baculoviruses are comprehensively described in (King L. A. and Possee R. D., The baculovirus expression system. A laboratory guide, Chapman & Hall, London, New York, Tokyo, Melbourne, Madras, 1992). This reference includes procedures for the following standard methods: preparation of insect culture media and maintenance of insect cell lines, propagation, titration and plaque purification of AcMNPV in cell culture, production and selection of recombinant baculoviruses by dot-blot hybridization or by using PCR techniques, characterization of recombinant baculoviruses, including extraction of DNA and its analysis, extraction of proteins produced in insect cells and their analysis in SDS-PAGE. For convenience herein, the abbreviations of the names of molecular chaperones will be used to designate transfer vectors and the corresponding recombinant baculovirus and expression products.

Example 1

Construction of an EGT Transfer Vector (AB-EGT)

Figure 2:
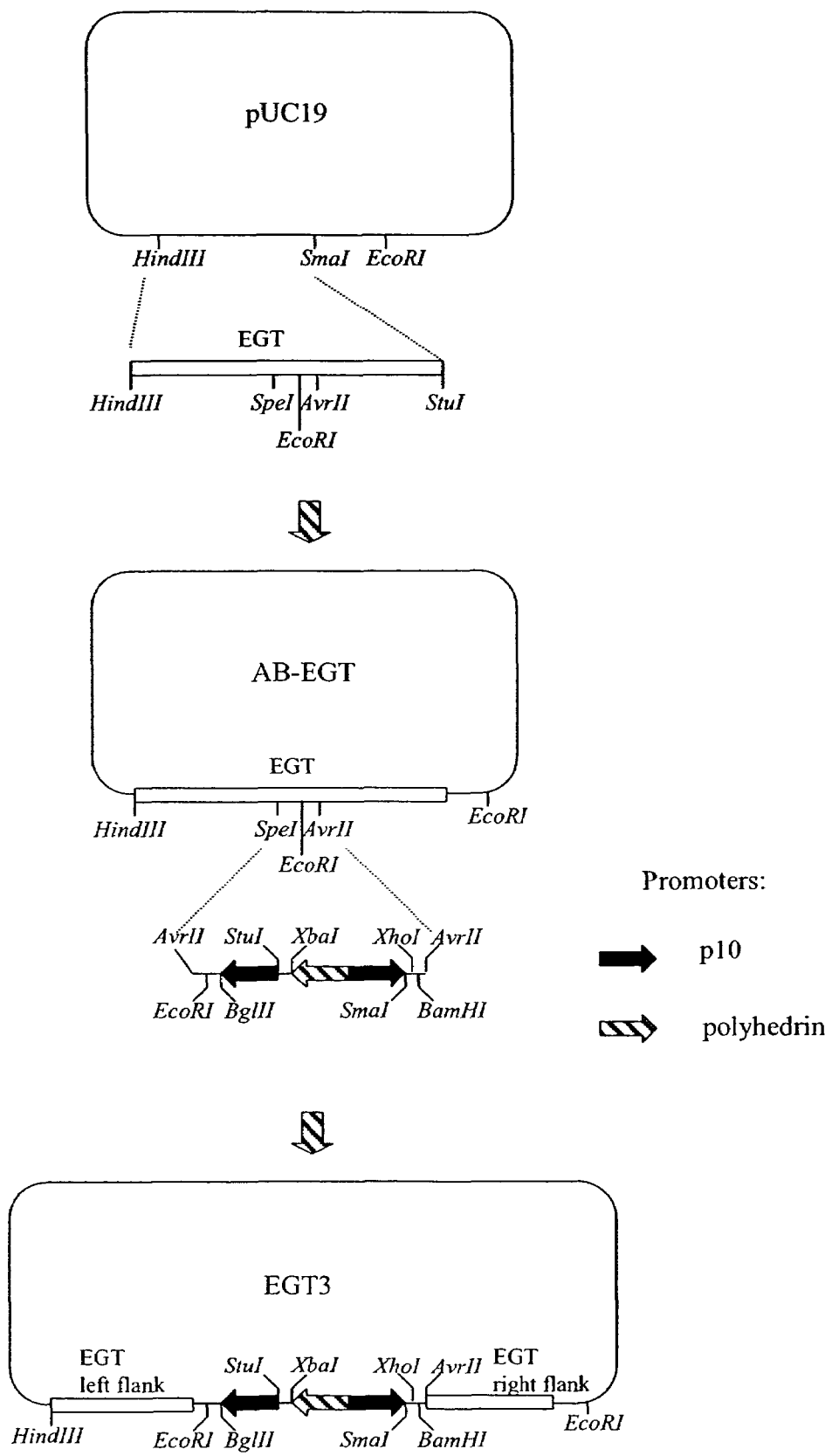
FIG. 2 shows the construction of the EGT3 plasmid transfer vector for the provision of 3 promoters into AB-EGT vector in order to facilitate expression of up to 3 polynucleotide sequences of interest.

To construct EGT transfer vector according to present invention, a DNA fragment comprising EGT gene polynucleotide sequence is cloned into the pUC19 plasmid vector (Acc#X02514) cleaved with HindIII and SmaI restriction endonucleases (FIG. 2). The EGT gene can be obtained from AcNMPV DNA (Acc#NC_001623, Smith G. E. and Summers, M.D., U.S. Pat. No. 4,879,236, 1987) or any of its derivatives, for example BacPAK6 recombinant baculovirus vector DNA (Kitts P. et al., Biotechniques, 14: 810–817, 1993) or Bac-to-Bac, Bac-N-Blue, BaculoDirect vector DNA (Invitrogen, Carlsbad, Calif.). BacPAK6 DNA is available from several sources, for example Pharmingen (San Diego, Calif.), Clontech (Palo Alto, Calif.), Orbigen, (San Diego, Calif.). Alternatively, any other baculovirus DNA containing EGT gene can be used for this purpose. Primers, complementary to opposite strands of the baculovirus DNA are selected in order to provide for amplification of EGT polynucleotide sequence in PCR. For example AcMNPV EGT gene is amplified using the following two primers:

[SEQ ID NO:1]
5'-GCGCAAGCTTGCAGCATGTTAAGTTTGGCG-3'

Restriction endonuclease sites can be provided at both ends of the PCR product to facilitate its cloning into the plasmid vector. HindIII site is provided in one of the primers (underlined) and StuI site is endogenous in the AcMNPV DNA and situated in the PCR product in vicinity of the DNA sequence homologous to the second primer (Acc#NC_001623). The amplified PCR product is digested at both ends with HindIII and StuI restriction endonucleases and inserted into HindIII-SmaI site to yield an EGT transfer vector designated AB-EGT (FIG. 1A). A polynucleotide sequence of interest can be conveniently cloned into this vector using unique SpeI or AvrII restriction sites situated in the EGT coding region. A polynucleotide sequence containing additional cloning sites can be inserted in the SpeI and/or AvrII sites. An alternative way to provide a convenient cloning site in the backbone insertion vectors it to mutate baculovirus DNA sequence in order to generate a convenient insertion site. Such site may include restriction endonuclease sites, such as SbfI site or any other specific sites useful for convenient cloning, for example a recombination site for employing GATE technology. Next, AB-EGT vector containing a polynucleotide sequence of interest is co-transfected into Sf9 cells with AcMNPV DNA or its derivative, and the polynucleotide sequence of interest is recombined into the baculovirus DNA. The inserion of the polynucleotide sequence of interest is achieved specifically in the same site(s) as in the AB-EGT vector. The co-transfection, plaque purification and selection of recombinant baculoviruses is performed in accordance with conventional methods (King L. A. and Possee R. D., The baculovirus expression system. A laboratory guide, Chapman & Hall, London, New York, Tokyo, Melbourne, Madras, 1992).

Example 2

Multiple EGT Transfer Vector (EGT3)

Multiple expression vectors are desirable when there is a need to facilitate expression of several genes in the same vector. This example describes insertion of 3 promoters into AB-EGT vector in order to facilitate expression of up to 3 polynucleotide sequences of interest. Expression of a polynucleotide sequences of interest can be achieved using EGT promoter resident in the EGT vectors. However, employment of much stronger promoters, such as polyhedrin, p10 or a basic protein promoter is preferred (Bonning B. C. et al., J. Gen. Virol., 75 (Pt 7):1551–1556, 1994). If the same promoter is employed twice in the same cassette, it is preferred that its copies are facing in opposite directions, more preferably away from each other. This is done in order to avoid unstable direct polynucleotide sequence repeats and to minimize interference between transcription complexes moving along the DNA molecule.

A promoter cassette containing 3 promoters (2 copies of p10 promoter facing in opposite direction, a copy of polyhedrin promoter, convenient cloning sites specific to each promoter, and transcription termination signals is derived from the previously described polyhedrin transfer vector pAcAB3 (Belyaev A. S. and Roy P. Nucleic Acids Res., 21:1219–1223, 1993). The promoter cassette is amplified in PCR using following primers:

[SEQ ID NO:3]
5'-GCGCACCTAGGTTGCTGATGATCCAGCATG-3'

[SEQ ID NO:4]
5'-CGCGCCTAGGCTCGAGTACTAATAACCGGATCCCCG-3'

AvrII restriction endonuclease sites (underlined) are provided in both primers. The amplified PCR product is digested at the ends with AvrII restriction endonucleases and inserted into AvrII and SpeI digested AB-EGT vector to yield an EGT transfer vector designated EGT3. Orientation of the promoter cassette is established using restriction analysis with BamHI and EcoRI restriction endonucleases. A plasmid vector with an opposite orientation of the promoter cassette was also obtained (EGT3R) and proved to be functional, however EGT3 vector was used in most of the experiments and in subsequent vector modifications.

Up to 3 proteins of interest can be expressed using EGT3 vector. However EGT3 or EGT3R vectors can be further modified to express more proteins by inserting additional promoters, for example basic protein promoter, or adding IRES elements, for example an IRES element derived from the cricket paralysis virus (Wilson J. E. et al., Mol Cell Biol., 20:4990–4999, 2000). The main utility of this vector is to express one or more proteins of interest. However, its utility is not limited to protein expression, but may involve synthesis of RNA molecules with regulatory or enzymatic activity, for example rybozymes. It can be also used to express specific sets of tRNA molecules. Different organisms have different codon usage characteristics. Due to this factor, some foreign genes may be poorly expressed in the baculovirus system as insect cells may have different codon preference. However, this can be amended by expressing tRNA specific to the codons underrepresented in insect cells, but abundant in a foreign gene(s). Therefore, EGT3 and other baculovirus plasmid transfer vectors can be used to improve production of proteins of interest, if their genes contain codons which are rarely used in the insect cells. Multiple expression vectors are preferred as organisms typically differ in more than one codon preference. Multiple expression vectors are also preferred for expression of molecular chaperones, as they act in ensembles. Backbone insertion vectors are preferred in both cases as it leaves traditionally used polyhedrin site for expression of a protein of interest. Though a protein of interest can be expressed to a high level in other sites, reserving polyhedrin site for this purpose is preferred, since very convenient vectors providing close to 100% efficiency selection techniques for this site were already developed. Thus, sets of tRNA genes or/and sets of genes encoding molecular chaperones characteristic for a particular class of organisms can be inserted into the backbone sites and provide for specific improvement in expression/folding of mammalian, or plant, or reptile, or arthropod, etc. proteins encoded at the polyhedrin site.

Example 3

EGT Transfer Vector with a Reporter Gene (EGT3-GFP)

Figure 3:
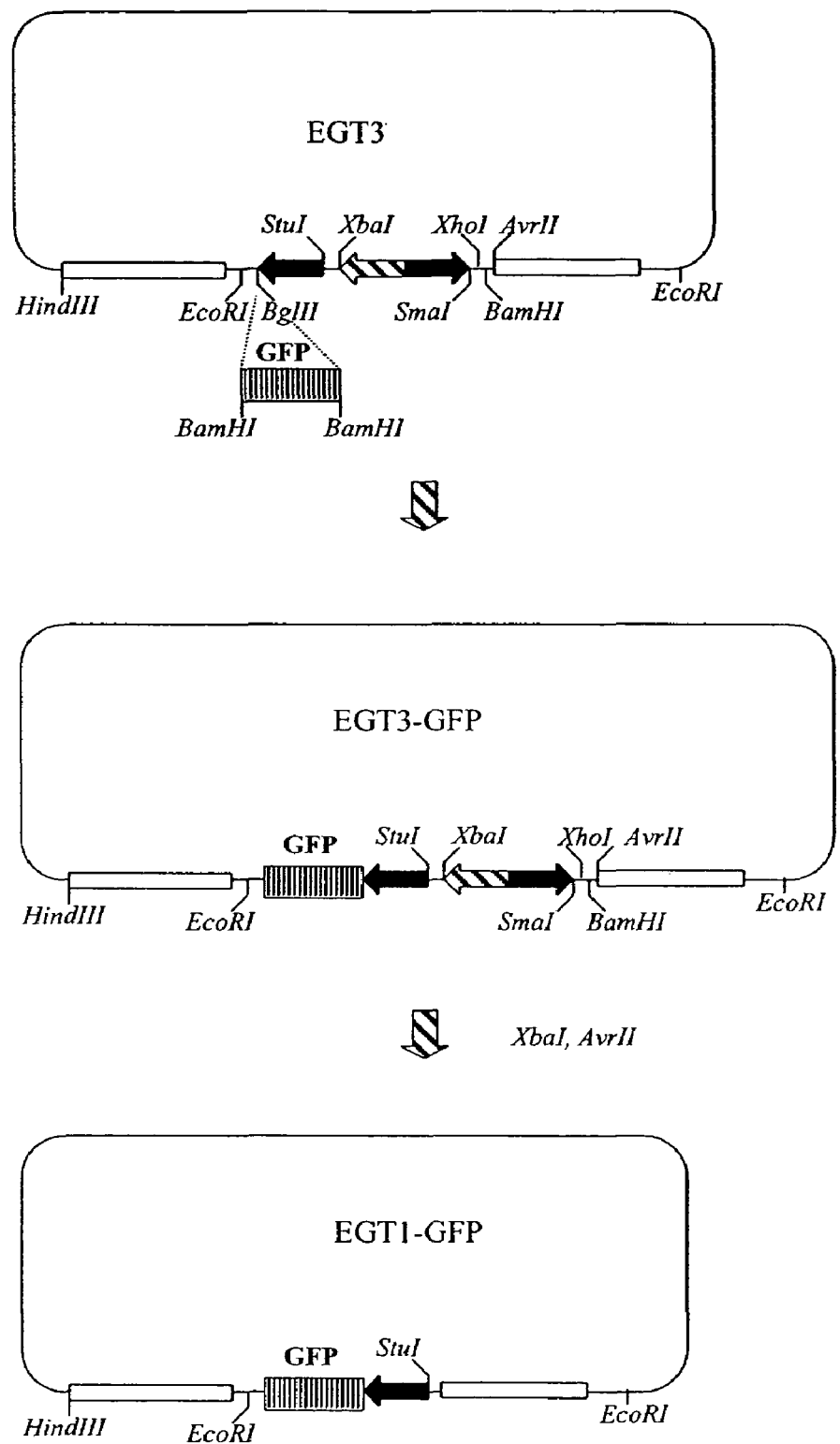
FIG. 3 shows the construction of plasmid transfer vectors EGT1-GFP and EGT3-GFP encoding a reporter green fluorescent protein.

This example describes insertion of a polynucleotide sequence of interest, which facilitates selection of recombinant baculoviruses obtained by recombination with a backbone plasmid transfer vector. More specifically, it describes insertion of such polynucleotide sequence into the EGT3 transfer vector, and more specifically, insertion of a gene encoding for a reporter protein, such as GFP (FIG. 3). A GFP gene, derived from jellyfish *Aequeorea victoria*, is amplified in PCR from a DNA containing such gene. Plasmid DNA containing this gene is available from Columbia University, New York or it can be purchased from commercial sources, for instance pGFP plasmid available from (Clontech, Palo Alto, Calif.). DNA containing GFP gene is amplified in PCR using following primers:

[SEQ ID NO:5]
5'-GCGCGGATCCAAAAAATGAGTAAAGGAGAAGAACTTTTCACTGG-3'

[SEQ ID NO:6]
5'-GCGCGGATCCTCTTTGTATAGTTCATCCATGCCATGTG-3'

Figure 1B:
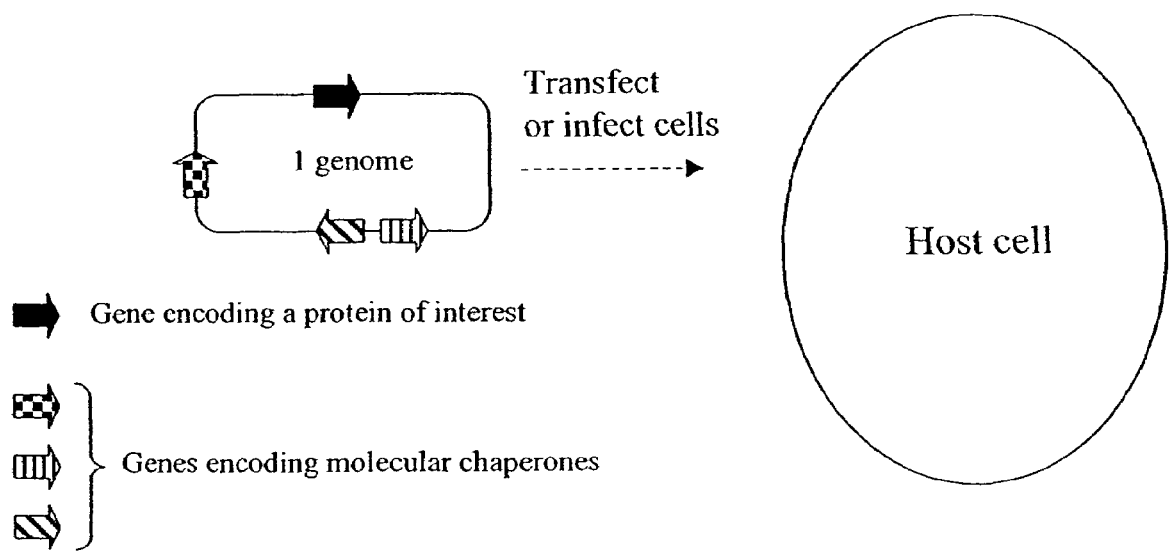

BamHI restriction endonuclease site (underlined) is provided in both primers. The amplified PCR product is digested at the ends with BamHI restriction endonuclease and inserted into BglII site of the EGT3 vector to yield an EGT transfer vector designated EGT3-GFP (FIG. 1B). Orientation of the GFP gene is established by restriction analysis using double digestion with StyI and AvrII restriction endonucleases and confirmed by DNA sequencing. Similarly, a plasmid vector EGT3R-GFP is obtained by inserting the same PCR fragment into the BglII site of EGT3R.

Example 4

Changing the Number of Transcription Units in an EGT Vector

The number of elements regulating transcription initiation can be increased or decreased depending on the requirements of experiment. Additional promoters can be added, for example a promoter cassette containing 4 promoters can be derived from the previously described plasmid transfer vector pAcAB4 using primers SEQ ID NO: 1 and SEQ ID NO:2 and inserted into the AB-EGT vector. Other promoters can be added, for example basic promoter can be derived using PCR technique from AcMNPV DNA and cloned into EGT vectors. One or more IRES elements, such as cricket paralysis virus IRES element can be inserted in lieu of one or more promoters in order to obtain additional transcription unit(s) encoding additional gene(s) from the same promoter (Wilson J. E. et al., Mol Cell Biol., 20:4990–4999, 2000; He X. S. et al., Gene, 175:121–125, 1996).

Likewise, the number of the transcription units can be reduced, which may be desirable to increase expression level of a particular protein product.

In this example, the number of transcription units in EGT3-GFP and EGT3R-GFP vectors was reduced by deleting 2 promoters in each of these vectors (FIG. 3). This was achieved by digesting EGT3-GFP vector with XbaI and AvrII restriction endonucleases and re-ligating the largest DNA fragment at the generated compatible sticky ends using T4 DNA ligase. The resulting vector was designated EGT1-GFP. Similarly, EGT3R-GFP vector was digested with SmaI and StuI restriction endonucleases and relegated at the generated blunt ends. The resulting vector was designated EGT1R-GFP. Each of the EGT3-GFP, EGT3R-GFP, EGT1-GFP and AGT1R-GFP were co-transfected with BacPAK6 baculovinis vector DNA and recombinant baculovirus clones are selected and plaque purified as set forth in the EXAMPLE 5. The generated recombinant baculoviruses are used to infect sub-confluent monolayers of Sf9 cells at m.o.i. 5 per cell and incubated for 48 hours at 27 C. Expression of GFP was examined as green fluorescence of the infected cells under ultraviolet light excitation wavelength 395 nm. Common UV transilluminators with the excitation wavelength 365 nm, such as Ultra-Lum available from VWR can be routinely used.

Apparently, expression of the GFP protein did not depend on the orientation of its transcription unit regarding the EGT gene, however it was dependent on the number of adjacent strong transcription units, as cells infected with EGT1-GFP and EGT1R-GFP recombinant baculoviruses exhibited about 60–80% higher fluorescence than cells infected with EFT3-GFP or EGT3R-GFP recombinant baculoviruses.

Example 5

Selection of GFP Positive Recombinant Baculoviruses

A plasmid transfer vector containing a GFP gene under the control of a strong baculovirus promoter is co-transfected with appropriate baculovirus DNA into suitable host cells. For example, EGT1-GFP plasmid transfer vector is co-transfected with BacPAK6 DNA into Sf9 cells. The resulting mixture of recombinant and non-recombinant baculoviruses is used to infect monolayers of Sf9 cells in order to generate individual plaques. The virus generated from each individual plaque is used to infect about 50% confluent monolayers of Sf9 cells growing in 24-well plates. The plates are incubated for 4 days at 27 C, after which they are inspected for green fluorescence under the ultraviolet light 365 nm. The viruses exhibiting GFP+ phenotype are subjected to several more rounds of plaque purification and propagation in 24-well plates and examination, until all of the wells in the plate exhibit GFP+ phenotype. The repeated rounds are necessary, since some GFP+ positive recombinants are generated by single-crossover events occurring only on one flank of the EGT vector and therefore can produce either GFP– revertants or stable GFP+ recombinants. Typically, 4–5 rounds are required to ensure generation and selection of stable double-crossover recombinants. Stable recombinants are further characterized by restriction analysis of their DNA (King L. A. and Possee R. D., The baculovirus expression system. A laboratory guide, Chapman & Hall, London, New York, Tokyo, Melbourne, Madras, 1992). Such characterization of the DNA of generated recombinants is particularly important if the recombinants are intended to be used as recombinant baculovirus vectors for expression of proteins of interest.

Example 6

Figure 4:
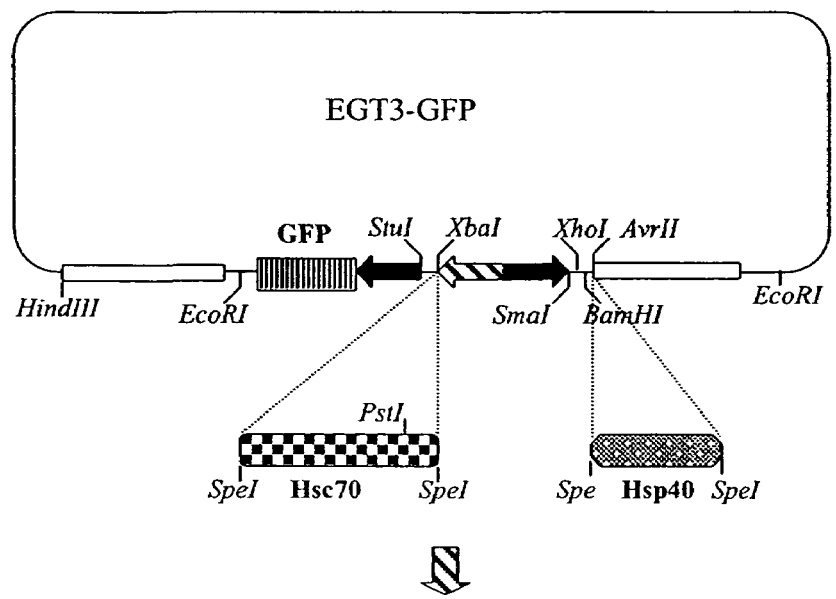
FIG. 4 shows the construction of the EGT3-GFP-70-40 construct that expresses green fluorescent protein, Hsc70, and Hsp40.
Figure 4:
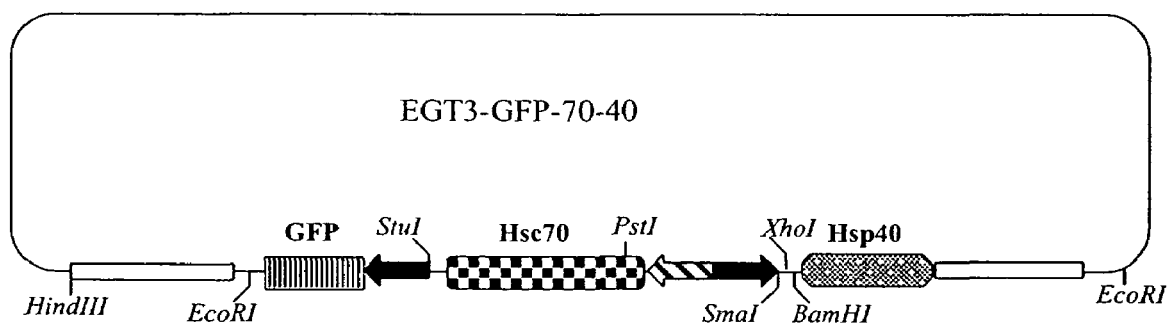

Generation of Recombinant Baculovirus Vectors Encoding Hsp40 and Hsc70 Molecular Chaperones This example describes insertion of genes encoding Hsp40 and Hsc70 molecular chaperones into the backbone of a baculovirus vector DNA, and leaving polyhedrin site available for expression of a gene of interest. To this end, a backbone plasmid transfer vector, for example an EGT transfer vector is constructed (FIG. 4).

cDNAs encoding molecular chaperones are generated by methods known to those skilled in the art. Common manipulations for generating cDNA libraries are described in (Current protocols in molecular biology. Ausubel et al., ed. Preparation and analysis of RNA. Construction of recombinant DNA libraries. John Wiley & sons, Inc. pub., 2000). cDNA libraries enriched for full-length cDNA are preferred (Zhu et al, Biotechniques, 30: 892–897, 2001). Commercially available human cDNA libraries from several tissues are available from Clontech, Palo Alto, Calif. Placenta or testis cDNA libraries are used, however other tissues could be used also, as chaperones are well represented in many tissues.

cDNA encoding Hsp40(dj2) is amplified in PCR using following primers:

[SEQ ID NO:7]
5'-CGCGCACTAGTAGAAGATGGTGAAAGAAACAACTTAC-3'

[SEQ ID NO:8]
5'-GCGCCACTAGTTAAGAGGTCTGACACTGAAGACC-3'

SpeI restriction endonuclease site (underlined) is provided in both primers. The amplified PCR product is digested at the ends with SpeI restriction endonuclease and inserted into AvrII site of the EGT3-GFP vector to yield an EGT transfer vector designated EGT3-GFP-Hsp40 (FIG. 4). Orientation of the Hsp40 gene is established by restriction analysis with EcoRI restriction endonuclease and confirmed by the DNA sequencing.

Next, cDNA encoding Hsc70 is amplified in PCR using following primers:

```
5'-                                        [SEQ ID NO:9]
GCGCACTAGTACACCCCAGCAACCATGTCCAAGGGACCTGCAGTTGG-3'

5'-                                        [SEQ ID NO:10]
CGCGACTAGTTAATCAACCTCTTCAATGGTGGGCCCCGAGGAAGCACC
ACC-3'
```

SpeI restriction endonuclease site (underlined) is provided in both primers. The amplified PCR product is digested at the ends with SpeI restriction endonuclease and inserted into SpeI site of the EGT3-GFP-40 vector to yield an EGT transfer vector designated EGT3-GFP-70-40 (FIG. 4). Orientation of the Hsc70 gene is established by analysis with HindIII restriction endonuclease and comfirmed by the DNA sequencing. During amplification, a T to C point mutation (bold and underlined) is introduced into the Hsc70 nucleotide sequence without causing change in the amino acid sequence of this protein. This mutation abolishes Bsu36.I site at the end of the Hsc70 coding sequence. This is necessary if the selection system for subsequent insertion of a gene of interest involves linearization of baculovirus DNA with Bsu.36.I restriction endonuclease, such as in BacPak6 (Clontec, Palo Alto, Calif.; Pharmingen, San Diego, Calif.) or BaculoDirect and Bac-N-Blue baculovirus vector DNA (Invitrogen, Carlsbad, Calif.). Any restriction endonuclease site has to be mutated in molecular chaperones coding sequence if it is subsequently employed in selection procedure using virus vector DNA linearization at such site, as the selection system characteristic for BacPAK6 vector is contingent on linearization of this DNA using Bsu36.I restriction endonuclease in the polyhedrin area. Otherwise simultaneous cleavage of vector DNA at the EGT site and in the polyhedrin area would render this selection unfeasible. This also applies to other vectors relying on linearization with Bsu36.I, such as Bac-N-Blue and BaculoDirect vector DNA (Invitrogen, Carlsbad, Calif.).

BacPAK6 DNA is co-transfected with EGT3-GFP-70-40 vector DNA and recombinant baculoviruses exhibiting GFP+ phenotype are selected, passaged, plaque purified and characterized as described in EXAMPLE 5. In addition to E. coli beta-galactosidaze resident in the polyhedrin site of the parental vector BacPAK6, the resulting recombinant baculovirus vector G-70-40 is expressing GFP as well as Hsc70 and Hsp40 molecular chaperones to a high level. However, expression of b-galactosidase resident in the polyhedrin site was only about 60% as compared to the parental vector BacPAK6. This is likely to be attributed to depletion of the cell resources due to undesirably high level of expression of Hsp40. Therefore, in the next example, expression of Hsp40 was reduced in order to achieve un-compromised expression of a protein of interest in the polyhedrin site.

Example 7

Adjustment of an Expression Level of a Molecular Chaperone

Level of expression of molecular chaperones can be adjusted to a desirable level. Chaperones interact in protein folding at certain ratios, which can be taken as an approximate guideline for the desired ratios of their expression using recombinant genomes. For example, in folding progesteron receptor, similar concentrations of Hsp70, Hsp90 and p23 were needed, however Hsp40 and Hop were effective at about 1/10 concentration of other proteins (Kosano, K. et al., J. Biol. Chem., 273: 32973–32979, 1998). A several times excess of Hsc70 over Hsp40 is typically required as the latter acts catalytically. Though, as will be discussed below, more than necessary Hsp40 did not adversely affect protein folding, overexpressing this protein beyond reasonable level is unlikely to benefit the expression system and may negatively impact on the available cell resources. This is the case with recombinant baculovirus vector G-70-40, where Hsp40 expression is several times higher than expression of Hsc70, whereas the reverse ratio is desirable.

G-70-40 recombinant baculovirus vector is essentially the same as parental BacPAK6 vector except it provides for expression of a reporter protein GFP and for expression of molecular chaperones Hsp40(dj2) and Hsc70. beta-galactosidase resides in the polyhedrin site of both vectors, however its expression was reduced in G-70-40 compared to BacPAK6 (see EXAMPLE 6).

Figure 5:
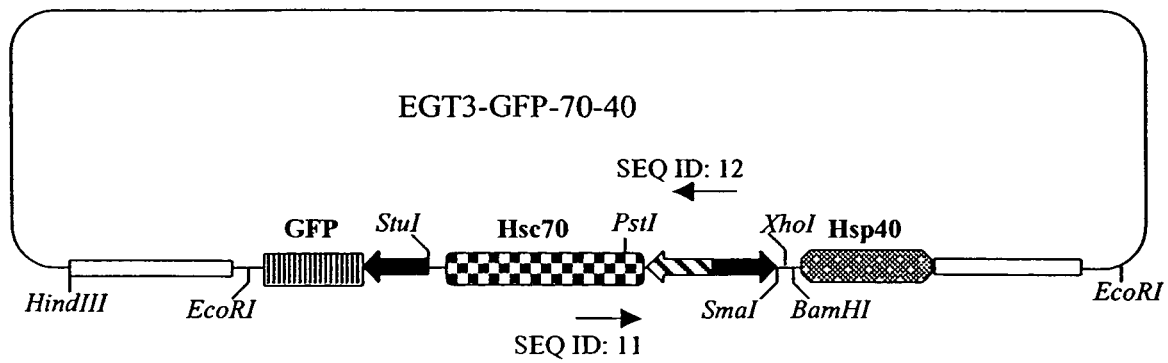
FIG. 5 shows the construction of the EGT3-GFP-70-40* construct that expresses green fluorescent protein, Hsc70, and Hsp40, but possesses a truncated p10 promoter.
Figure 5:
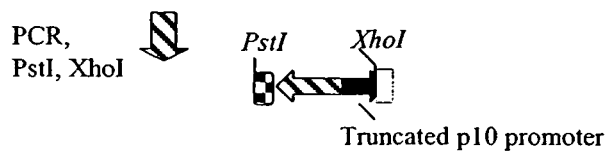
Figure 5:
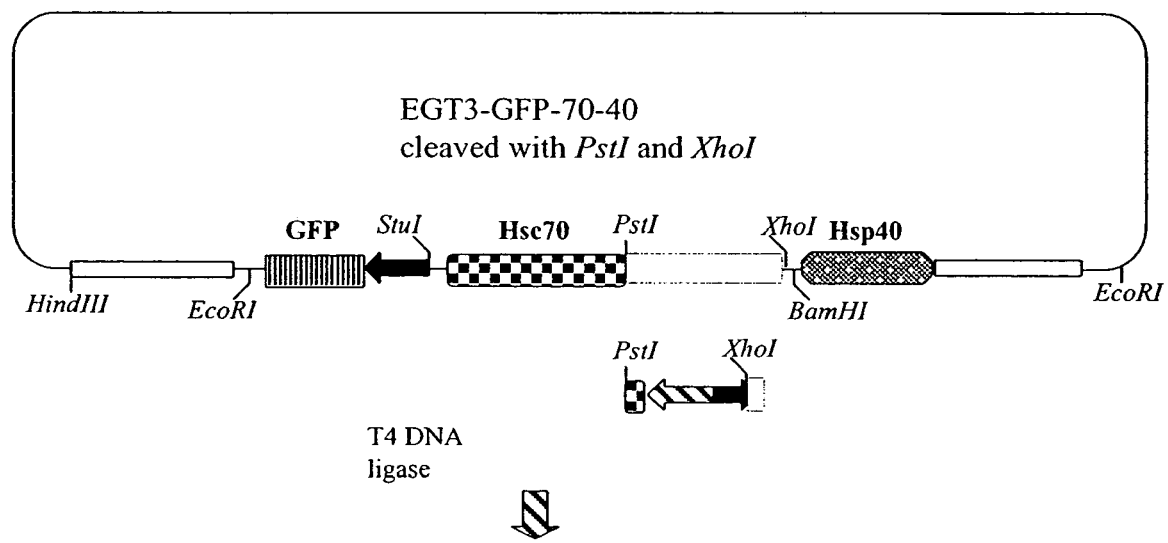
Figure 5:
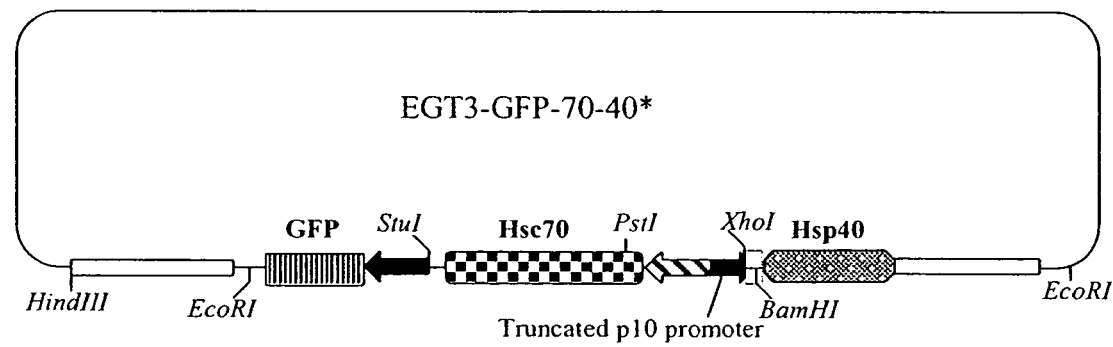

Weaker promoters can be used in order to reduce a molecular chaperone expression, or a strong promoter can be mutated or truncated as represented on FIG. 5. As was presented in EXAMPLE 6, Hsp40 gene was placed under the control of p10 promoter in the EGT3-GFP-70-40 plasmid transfer vector, which was used to generate G-70-40 recombinant baculovirus vector.

In order to truncate the promoter, EGT3-GFP-70-40 plasmid DNA is amplified in PCR using following primers:

```
                                           [SEQ ID NO:11]
5'-GCCAAGATCAATACCAACTGCAGG-3'

[SEQ ID NO:12]
5'-CGCGCTCGAGTAATTTACAGTATAGTATTTTAATTAATATAC-3'
```

In order to further truncate the promoter, EGT3-GFP-70-40 plasmid DNA is amplified in PCR using one of the previous primers [SEQ ID NO: 11] and the following primer:

```
                                           [SEQ ID NO:13]
5'-CGCGCTCGAGCAGTATAGTATTTTAATTAATATACAAATG-3'
```

XhoI sites are provided in the primers SEQ ID NO: 12 and 13 (underlined) and endogenous to the Hsc70 gene PstI site (underlined) is situated in the primer SEQ ID NO: 11. PCR products generated with both pairs of primers are digested at both ends with XhoI and PstI restriction endonucleases and inserted into XhoI and PstI digested EGT3-GFP-70-40 plasmid to yield EGT transfer vectors with truncated p10 promoter controlling expression of Hsp40. The p10 promoter generated using primer SEQ ID NO: 12 is truncated at position −14, (Weyer U. & Possee R. D., Nuc. Acids Res., 16: 3635–3653, 1988), and the resulting plasmid transfer vector was designated EGT3-GFP-70-4014. The p10 promoter generated using primer SEQ ID NO: 12 is truncated at position −23, and the resulting plasmid transfer vector was designated EGT3-GFP-70-4023.

BacPAK6 DNA was co-transfected with EGT3-GFP-Hsc70-Hsp4014 or EGT3-GFP-Hsc70-Hsp4023 plasmid transfer vector DNA. Recombinant baculoviruses exhibiting GFP+ phenotype were selected, passaged, plaque purified and characterized as described in EXAMPLE 5. Recombinant baculovirus vector produced with EGT3-GFP-70-4014 plasmid was designated G-70-40* and recombinant baculovirus vector DNA produced with EGT3-GFP-70-4023 was designated G-70-40**. As desired, in both vectors expression of beta-galactosidase was restored practically to the same level as in the parent vector BacPAK6. Both vectors expressed GFP and Hsc70 to a high level and expression of Hsp40 was reduced in both vectors. G-70-40* expressed Hsp40 still to a high level, and, as intended, it was lower than the level of expression Hsc70. However, the expression level of Hsp40 in G-70-40 was very low. The Hsp40 protein band was barely visible in the lysates of G-70-40-infected insect cells separated in SDS-polyacrylamide gels and stained with coomassie blue. Therefore, G-70-40* was selected for further experiments, as it provided for uncompromised expression of a protein of interest (beta-galactosidase) driven from the gene inserted into the polyhedrin site and provided for high level of expression of molecular chaperones and GFP.

Example 8

Figure 6:
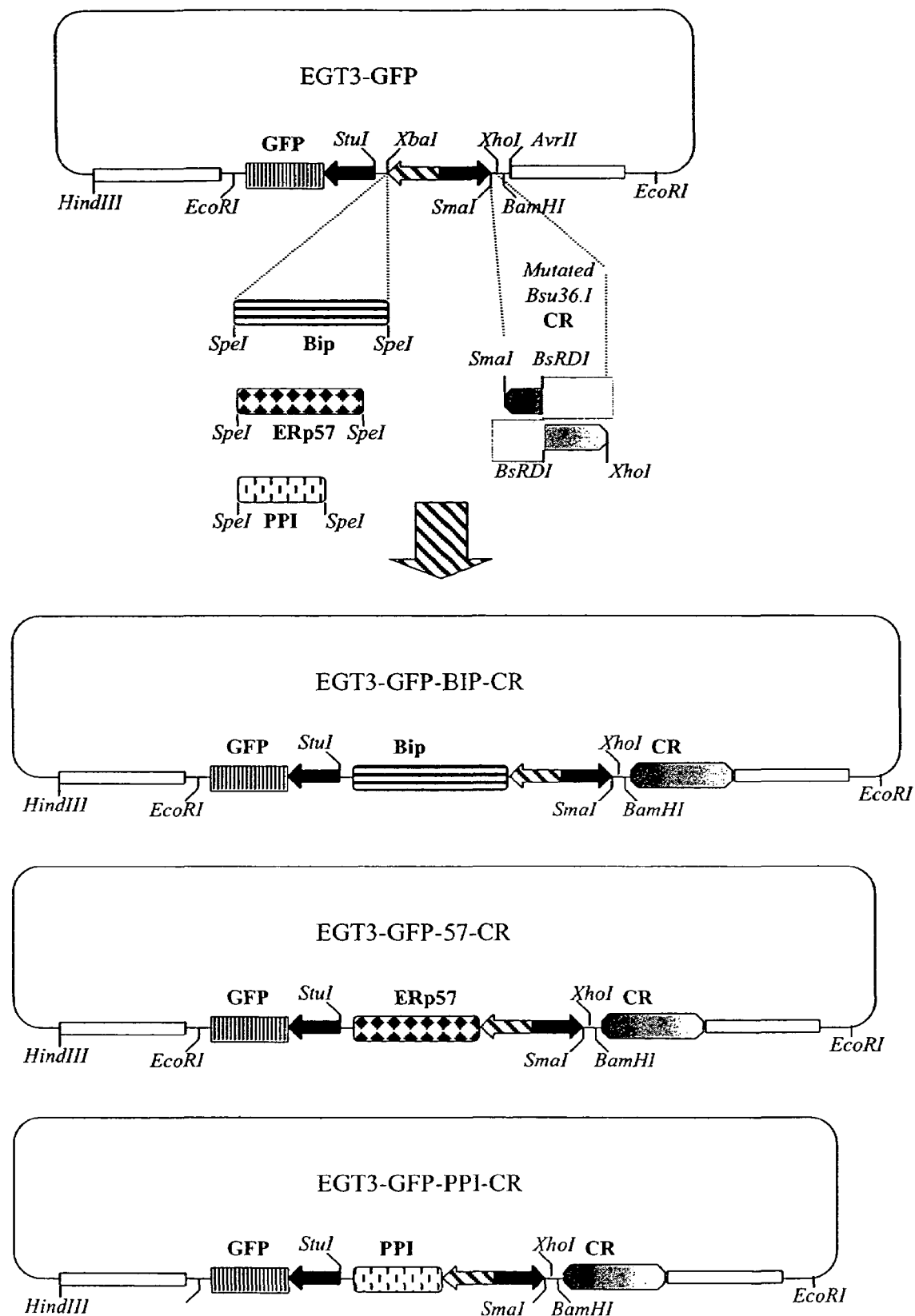
FIG. 6 shows the construction of several CR-containing expression vectors including: the EGT3-GFP-BIP-CR construct that expresses green fluorescent protein, Bip and calreticulum; the EGT3-GFP-57-CR construct that expresses green fluorescent protein, ERp57 and calreticulum; and the EGT3-GFP-PPI-CR construct that expresses green fluorescent protein, cyclophilin B and calreticulum.
Figure 7:
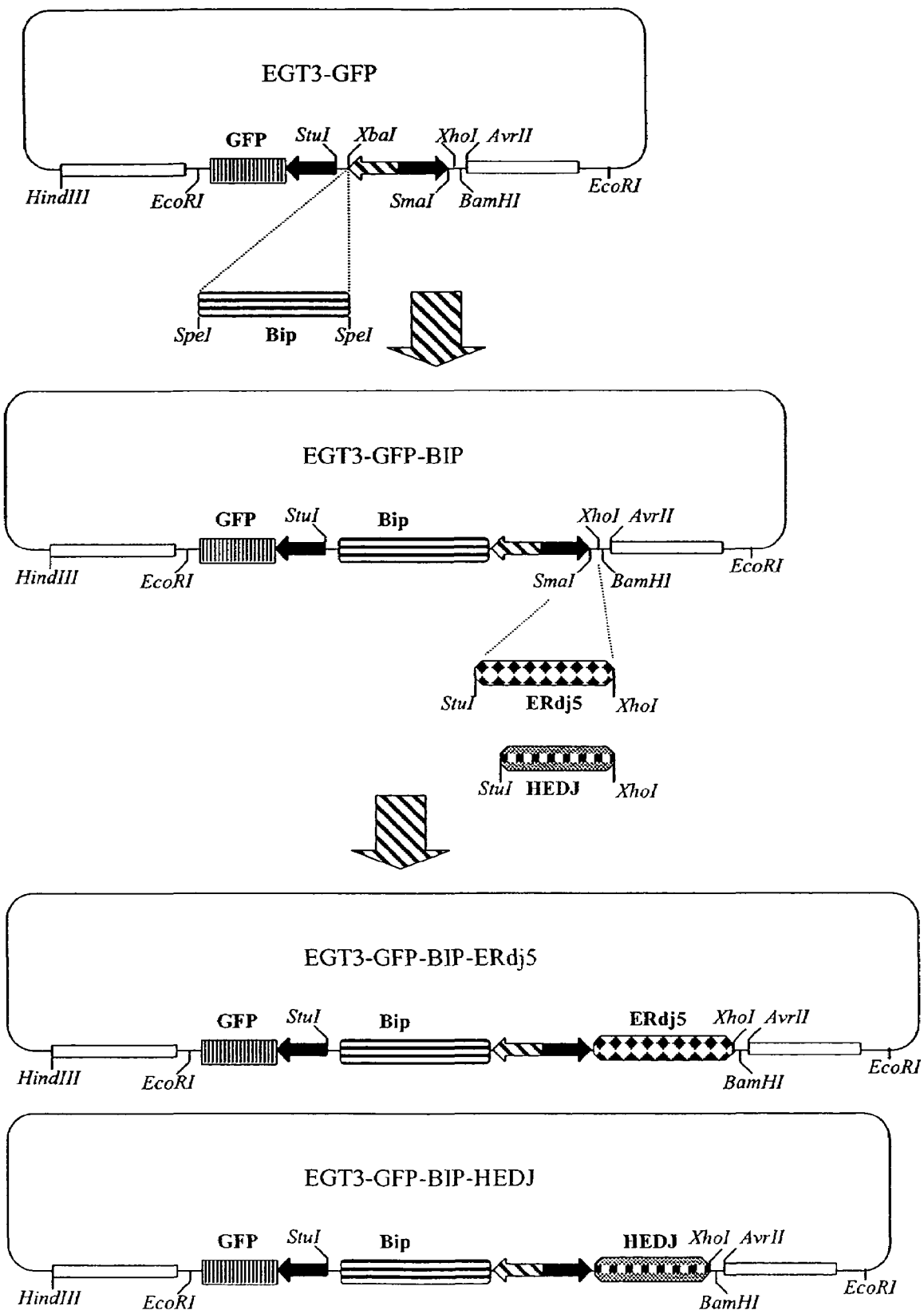
FIG. 7 shows the construction of two BIP-containing expression vectors including: the EGT3-GFP-BIP-ERdj5 construct that expresses green fluorescent protein, Bip and ERdj5 and the EGT3-GFP-BIP-HEDJ construct that expresses green fluorescent protein, Bip and HEDJ.

Generation of Recombinant Baculovirus Vectors Encoding Calreticulin, ERp57, BIP, PPI and PDI This example describes insertion of genes encoding different combinations of calreticulin, ERp57, Bip, PDI and PPI into the backbone of a baculovirus vector DNA (FIGS. 6, 7). Specifically, it describes insertion of chaperone genes into EGT site or EGT and p10 sites in the BacPAK6 vector DNA, whereas the polyhedrin insertion site remains available for insertion of a gene of interest using selection system characteristic for the BacPAK6 vector (Kitts P. et al., Biotechniques, 14: 810–817, 1993).

cDNAs encoding molecular chaperones are generated by methods known to those skilled in the art. Common manipulations for generating cDNA libraries are described in (Current protocols in molecular biology. Ausubel et al., ed. Preparation and analysis of RNA. Construction of recombinant DNA libraries. John Wiley & sons, Inc. pub., 2000). Commercially available human cDNA libraries from several tissues are available from Clontech, Palo Alto, Calif. Human placenta or testis cDNA libraries are used, however other tissues could be used also as chaperones are well represented in many cell types.

cDNA encoding calreticulin is amplified in PCR using two sets of following primers:

```
                                                     [SEQ ID NO:14]
5'-GCGTCCCGGGCCATGCTGCTATCCGTGCCGCT-3'

[SEQ ID NO:15]
5'-GCGCGCAATGGGGCTTGGAGTCTGTGGGATCATCGATCT-3'
```

This pair of primers is used for amplification of the first part of the gene:

```
                                                     [SEQ ID NO:16]
5'-CGCGCAATGCCGAGGACTGGGACAAGCCCGAGCAT-3'

[SEQ ID NO:17]
5'-CGCGCTCGAGCCTCTCTACAGCTCGTCCTTG-3'
```

This pair of primers is used for amplification of the remaining part of the gene.

The gene is amplified in two parts due to necessity of mutating the internal Bsu36.I site in the human calreticulin gene. Restriction sites (underlined) are provided in the primers. SmaI site is provided in the primer SEQ ID NO: 14, BsrDI sites are provided in the primers SEQ ID NO: 15 and 17, XhoI site is provided in the primer SEQ ID NO: 16.

The amplified PCR products are first digested at one end with BsrDI restriction endonuclease and ligated into a larger DNA fragment encoding complete calreticulin gene. Bsu36.I site is mutated in this gene as the primer SEQ ID NO: 16 and contains T to C point mutation (bold and underlined), which abolishes the Bsu36.I site without changing the encoded amino acid. The product of the ligation reaction is digested with SmaI and XhoI restriction endonucleases inserted into EGT3-GFP vector digested with the same enzymes to yield an EGT transfer vector designated EGT3-GFP-CR (FIG. 6).

The insertion of calreticulin gene is verified using digestion with SmaI and BamHI or XbaI and BamHI restriction endonucleases, as it has internal BamHI sites, and confirmed by the DNA sequencing.

Next, cDNA encoding PPI (cyclophilin B) is amplified in PCR using following primers:

```
                                                     [SEQ ID NO:18]
5'-GCGCACTAGTGGATGCTGCGCCTCTCCGAA-3'

[SEQ ID NO:19]
5'-CGCGAGGCCTACTCCTTGGCGATGGCAAAG-3'
```

SpeI restriction endonuclease sites (underlined) are provided in primer SEQ ID NO: 18.

StuI restriction endonuclease site (underlined) is provided in primer SEQ ID NO: 19. The amplified PCR product is digested at the ends with SpeI and StuI restriction endonucleases and inserted into EGT3-GFP-CR vector digested with the same enzymes to yield an EGT transfer vector designated EGT3-GFP-PPI-CR (FIG. 6). Insertion of the PPI gene is established by analysis with XbaI and BamHI restriction endonucleases and confirmed by the DNA sequencing.

Alternatively, CDNA encoding Bip is amplified in PCR using following set of primers:

```
5'-                                                  [SEQ ID NO: 20]
   GCGCACTAGTCAACTGGCTGGCAAGATGAAGCTCTCCCTGGTGGCC-3'

[SEQ ID NO: 21]
5'-GCGCACTAGTCTACAACTCATCTTTTTCTGCTGTATCCT-3'
```

SpeI restriction endonuclease site (underlined) is provided in both primers.

The amplified PCR product is digested at the ends with SpeI restriction endonuclease and inserted into EGT3-GFP-CR vector digested with the same enzyme to yield an EGT transfer vector designated EGT3-GFP-BIP-CR (FIG. 6). Insertion of the Bip gene is established by analysis with EcoRI restriction endonuclease and confirmed by the DNA sequencing.

Similarly, the same PCR product is digested at the ends with SpeI restriction endonuclease and inserted into EGT3-GFP vector digested with the same enzyme to yield an EGT transfer vector designated EGT3-GFP-BIP (FIG. 7). Insertion of the Bip gene is established by analysis with EcoRI restriction endonuclease and confirmed by the DNA sequencing. Next, EGT3-GFP-BIP vector is used to accept Bip cofactors ERdj5 or HEDJ.

CDNA encoding ERdj5 is amplified in PCR using following set of primers:

```
                                            [SEQ ID NO: 22]
5'-GCGCAGGCCTGCATAAGAAAGAGAATGGGAGTCTGGT-3'

[SEQ ID NO: 23]
5'-GCGCTCTAGAGGTGTCTTCTGATGTCATCTGTCAGA-3'
```

CDNA encoding HEDJ is amplified in PCR using following set of primers:

```
                                            [SEQ ID NO: 24]
5'-GCGCAGGCCTAACCATGGCTCCGCAGAACCTGA-3'

[SEQ ID NO: 25]
5'-GCGCCTCGAGCACTCTCAATATCCTTGCAGTCC-3'
```

StuI restriction endonuclease sites (underlined) are provided in the primers SEQ ID NO: 22 and 24. XbaI restriction endonuclease sites (underlined) are provided in the primer SEQ ID NO: 23 and 25. The amplified PCR products are digested at the ends with these restriction endonucleases and inserted into EGT3-GFP-CR vector digested with SmaI and XhoI to yield an EGT transfer vector designated correspondingly EGT3-GFP-BIP-ERdj5 and EGT3-GFP-BIP-HEDJ (FIG. 7). Insertion of ERdj5 and HEDJ genes is established by analysis with EcoRI and XhoI restriction endonucleases and confirmed by the DNA sequencing.

CDNA encoding ERp57 is amplified in PCR using following set of primers:

```
                                            [SEQ ID NO: 26]
5'-GCGCACTAGTAAAATGAGACTCCGCCGCCTAGCGCTGTT-3'

[SEQ ID NO: 27]
5'-GCGCACTAGTGCTTTAGAGATCCTCCTGTGCCTT-3'
```

SpeI restriction endonuclease sites (underlined) are provided in both primers. The amplified PCR product is digested with SpeI and restriction endonuclease and inserted into EGT3-GFP-CR vector digested with the same enzyme to yield an EGT transfer vector designated EGT3-GFP-57-CR (FIG. 6). Orientation of the ERp57 gene is established by analysis with AvrII restriction endonuclease and confirmed by the DNA sequencing.

In addition to BacPAK6 DNA, a derivative of this vector marketed as Sapphire (Orbigen, San Diego, Calif.) was also used with some of these transfer vectors. The Sapphire DNA is identical to BacPAK6 DNA except it contains human PDI gene, which was transferred into the p10 site using a p10 plasmid transfer vector. A DNA fragment which encodes PDI, was excised from pVLb plasmid transfer vector (Vuori K. et al., Proc. Natl. Acad. Sci. USA, 89: 7467–7470, 1992) using BglII and BamHI restriction endonucleases and cloned into BglII cut p10 plasmid transfer vector pAcUW1 (Weyer U. et al., J. Gen. Virol., 71:1525–1534, 1990).

Insertion of foreign genes into the p10 site was achieved using techniques recommended for this vector (Weyer U. et al., J. Gen. Virol., 71:1525–1534, 1990). In brief, the plasmid transfer vector DNA containing PDI gene under the control of p10 promoter is co-transfected with a baculovirus DNA linearized at the LacZ gene residing in the p10 site. The recombinants exhibiting LacZ minus phenotype are selected as white foci in the presence of X-gal. The DNA of this recombinant virus is purified and co-transfected with a plasmid transfer vector containing lacZ gene and three Bsu36.I sites in the polyhedrin site area as described (Kitts P. et al., Biotechniques, 14: 810–817, 1993). This DNA was designated BacPAK6-PDI. Due to expression of PDI, this baculovirus vector and recombinants obtained using this vector are exhibiting longer time of protein production, since cells infected with recombinant baculoviruses expressing PDI survive about 12 hours longer.

BacPAK6 or BacPAK6-PDI DNA is co-transfected with EGT3-GFP-CR, EGT3-GFP-PPI-CR, EGT3-GFP-BIP, EGT3-GFP-BIP-CR, EGT3-GFP-BIP-ERdj5, EGT3-GFP-BIP-HEDJ and EGT3-GFP-57-CR transfer vector DNA and recombinant baculoviruses exhibiting GFP+phenotype are selected, passaged, plaque purified and characterized as described in EXAMPLE 5.

The viruses are designated as follows:

generated with BacPAK6 and EGT3-GFP-CR was designated G-CR, generated with BacPAK6 and EGT3-GFP-57-CR was designated G-57CR, generated with BacPAK6 and EGT3-GFP-BIP-CR was designated G-BIP-CR, generated with BacPAK6 DNA and EGT3-GFP-BIP was designated G-BIP, generated with BacPAK6 DNA and EGT3-GFP-BIP-ERdj5 was designated G-BIP-ERdj5, generated with BacPAK6-PDI DNA and EGT3-GFP-BIP designated G-BIP-HEDJ, generated with BacPAK6-PDI and EGT3-GFP-CR was designated G-CR-PDI, generated with BacPAK6-PDI and EGT3-GFP-BIP was designated G-BIP-PDI, generated with BacPAK6-PDI and EGT3-GFP-PPI-CR was designated G-PPI-CR-PDI, generated with BacPAK6-PDI and EGT3-GFP-BIP-CR was designated G-BIP-CR-PDI, generated with BacPAK6-PDI and EGT3-GFP-57-CR was designated G-57-CR-PDI generated with BacPAK6-PDI DNA and EGT3-GFP-BIP-ERdj5 was designated G-BIP-ERdj5-PDI, generated with BacPAK6-PDI DNA and EGT3-GFP-BIP-HEDJ designated G-BIP-HEDJ-PDI.

Most of the molecular chaperones were expressed well, and expression of beta-galactosidase in the polyhedrin site is close to the level of expression in the parental vector BacPak6 except for the G-PPI-CR-PDI. The yield of the recombinant virus G-PPI-CR-PDI was also only about 40% of the virus yield characteristic for a parental BacPAK6-PDI virus. The phenomenon appears to be specific to PPI, as other vectors did not have this problem. It is unlikely to be due to the depletion of the cell resources, as expression of PPI was moderate. This could be due to toxicity of PPI to insect cells, as Sf9 cells infected with G-PPI-CR-PDI exhibited unusual vacuolization of the cytoplasm. Other recombinant viruses generated in this example have about the same virus yields as their parental viruses.

Example 9

Helper Viruses for Providing Molecular Chaperones in Co-Infection

Though it is preferable to provide as many chaperones as possible in the same genome with the protein of interest, vectors containing all the desired chaperones may not be available. Therefore, additional chaperones can be provided using helper viruses in co-infection with a virus expressing a protein of interest, which may or may not also express molecular chaperones. Providing molecular chaperones in the same genome with the protein of interest and also providing them in the helper viruses ensures certain versatility, where depending on the m.o.i., on average more or less molecular chaperone can be delivered into a host cell. In one embodiment, recombinant baculoviruses which express misfolded proteins of interest can be screened for appropriate chaperones, which improve protein folding using co-infection with helper viruses which provide different sets of molecular chaperones. Based on these studies, additional molecular chaperones can be inserted into the backbone of the baculovirus vectors.

cDNA encoding molecular chaperones are generated by methods known to those skilled in the art. Common manipulations for generating cDNA libraries are described in (Current protocols in molecular biology. Ausubel et al., ed. Preparation and analysis of RNA. Construction of recombinant DNA libraries. John Wiley & sons, Inc. pub., 2000.). cDNA libraries enriched for full-length cDNA are preferred. Commercially available human cDNA libraries from several tissues are available from Clontech, Palo Alto, Calif. Placenta or testis cDNA libraries are used, however other tissues could be used also as chaperones are well represented in many of the tissues. Backbone vectors; as well as polyhedrin transfer vectors, for example pVL1393 available from Pharmingen or Orbigen (San Diego, Calif.), can be used to construct helper viruses expressing molecular chaperones. Multiple polyhedrin transfer vectors, for example pACAB3, pAcAB4, pAcUW1, EGT3, EGT3-GFP can be used to express several chaperones in one helper virus.

cDNA encoding Hsp90 is amplified in PCR using following primers:

[SEQ ID NO: 28]
5'-GCGCAGATCTAAAATGCCTGAGGAAGTGCACCA-3'

[SEQ ID NO: 29]
5'-GCGCAGATCTAATCGACTTCTTCCATGCGAGA-3'

Figure 8:
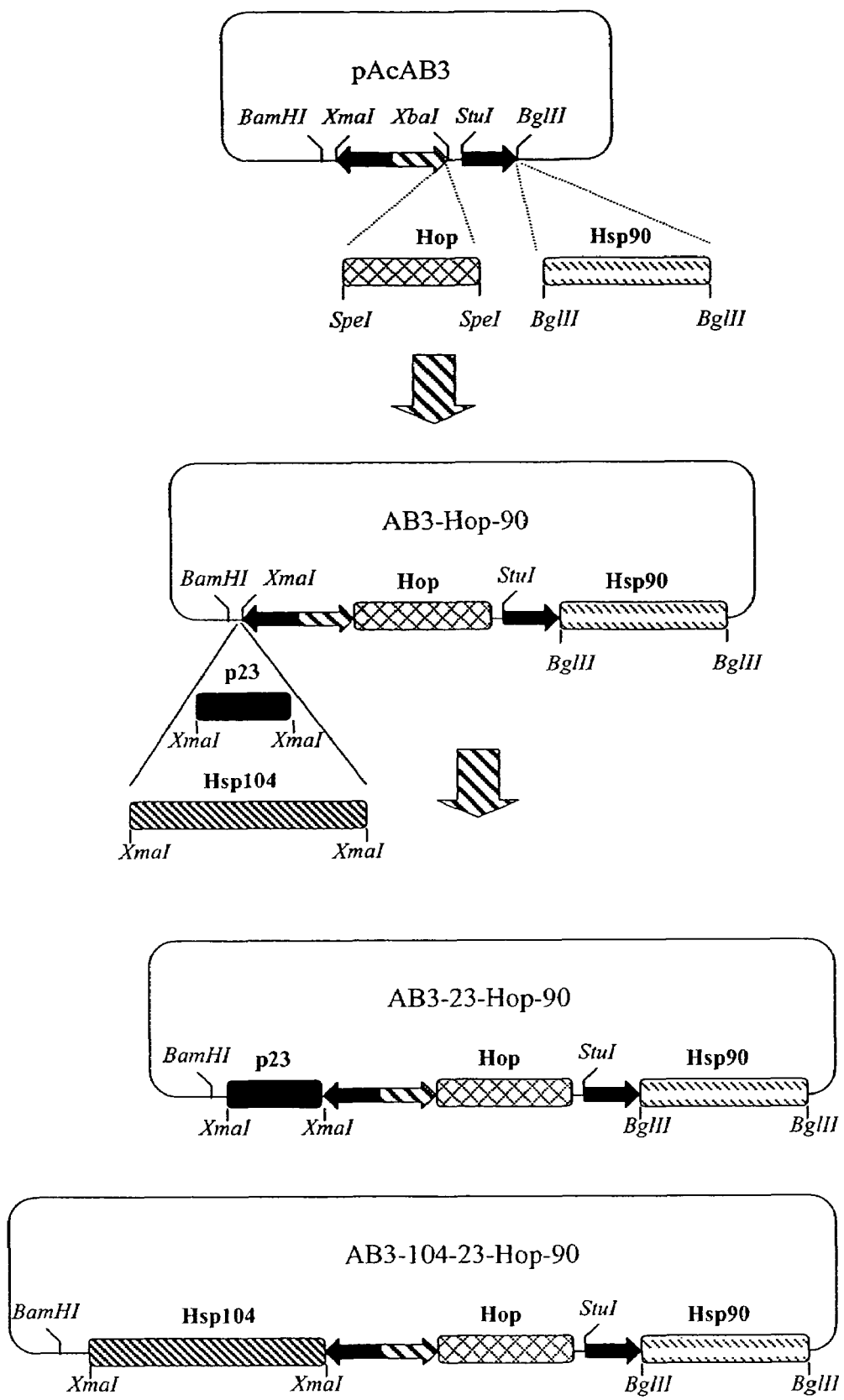
FIG. 8 shows the construction of two Hop-90-containing expression vectors including: the AB3-23-Hop-90 construct that expresses Hop, Hsp90 and p23 and the AB3-104 23-Hop-90 construct that expresses Hop, Hsp90 and Hsp104.

BglII restriction endonuclease sites (underlined) are provided in both primers. The amplified PCR product is digested at the ends with BglII restriction endonuclease and inserted into BglII site of the pAcAB3 vector to yield AB3-90 plasmid transfer vector (FIG. 8). Orientation of the Hsp90 gene is established by restriction analysis with StuI and EcoRI restriction endonucleases and confirmed by the DNA sequencing.

cDNA encoding Hop is amplified in PCR using following primers:

[SEQ ID NO: 30]
5'-GCGCACTAGTAAAATGGAGCAGGTCAATGAGCTGAAGGAGAAA-3'

[SEQ ID NO: 31]
5'-GCGCACTAGTCATCACCGAATTGCAATCAGACCCAGAT-3'

Figure 9:
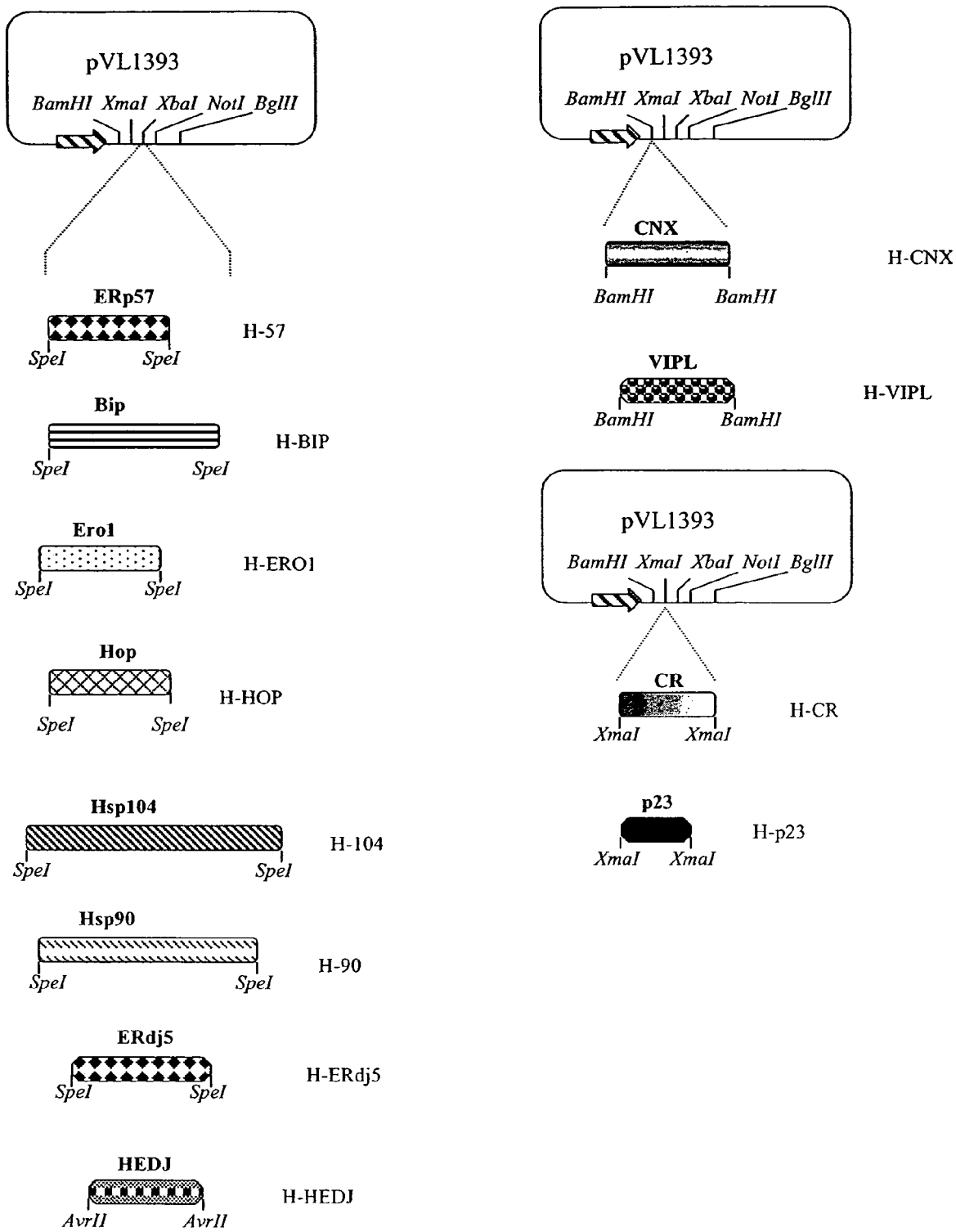
FIG. 9 shows the construction of transfer vector pVL1393 with a variety of molecular chaperone polynucleotides encoding for: ERp57, Bip, Ero1, Hop, Hsp104, Hsp90, ERdj5, HEDJ, calnexin, VIPL, calreticulin, and p23.

SpeI restriction endonuclease sites (underlined) are provided in both primers. The amplified PCR product is digested at the ends with SpeI restriction endonuclease and inserted into XbaI site of the pVL1393 vector to yield a polyhedrin transfer vector designated pVL-Hop (FIG. 9). Orientation of the Hop gene is established by restriction analysis with BglII restriction endonuclease and confirmed by the DNA sequencing. The same PCR fragment is also inserted into XbaI site of the AB3-90 vector to yield AB3-Hop-90 plasmid transfer vector (FIG. 8). Orientation of the Hop gene is established by restriction analysis with BglII restriction endonuclease and confirmed by the DNA sequencing.

cDNA encoding p23 is amplified in PCR using following primers:

[SEQ ID NO: 32]
5'-GCGCCCCGGGTTCACAATGGAGCCTGCTTCTGCA-3'

[SEQ ID NO: 33]
5'-GCGCCCCGGGATATTCCTTACTCCAGATCTGGCAT-3'

XmaI restriction endonuclease sites (underlined) are provided in both primers. The amplified PCR product is digested at the ends with XmaI restriction endonuclease and inserted into XmaI site of the pVL1393 vector to yield a polyhedrin transfer vector designated pVL-23 (FIG. 9). Orientation of the p23 gene is established by restriction analysis with HindIII restriction endonuclease and confirmed by the DNA sequencing. The same PCR fragment is also inserted into XmaI site of the AB3-Hop-90 vector to yield AB3-23-Hop-90 plasmid transfer vector (FIG. 8). Orientation of the Hop gene is established by restriction analysis with BglII restriction endonuclease and confirmed by the DNA sequencing.

cDNA encoding Ero1 is amplified in PCR using following set of primers:

[SEQ ID NO: 34]
5'-GCGCACTAGTGCGCACTAGTAAAATGGGCCGCGGCTGGGGATTCTTGTTT-3'

[SEQ ID NO: 35]
5'-GCGCACTAGTTAATGAATATTCTGTAACAAGTTCCTGAAGT-3'

SpeI restriction endonuclease sites (underlined) are provided in both primers. The amplified PCR product is digested at the ends with SpeI restriction endonuclease and inserted into XbaI site of the pVL1393 vector to yield a polyhedrin transfer vector designated pVL-Ero1. Orientation of the Ero1 gene is established by restriction analysis with HindIII, EcoRI or EcoRV restriction endonucleases and confirmed by the DNA sequencing.

CDNA encoding HEDJ is amplified in PCR using following set of primers:

[SEQ ID NO: 36]
5'-GCGCCCTAGGAACCATGGCTCCGCAGAACCTGA-3'

[SEQ ID NO: 37]
5'-GCGCCCTAGGCACTCTCAATATCCTTGCAGTCC-3'

AvrII restriction endonuclease sites (underlined) are provided in both primers. The amplified PCR product is digested at the ends with AvrII restriction endonuclease and inserted into XbaI site of the pVL1393 vector to yield a polyhedrin transfer vector designated pVL-Ero1.

cDNA encoding VIPL is amplified in PCR using following primers:

[SEQ ID NO: 38]
5'-GCGCGGATCCAAAGATGGCGGCGACTCTGGGA-3'

[SEQ ID NO: 39]
5'-GCGCGGATCCTCAGTAGAAGCGCTTTCGGCT-3'

BamHI restriction endonuclease sites (underlined) are provided in both primers. The amplified PCR product is digested at the ends with BamHI restriction endonuclease and inserted into BamHI site of the pVL1393 vector to yield a polyhedrin transfer vector designated pVL-VIPL. Yeast Saccharomyces cerevisiae Hsp104 is amplified from yeast genomic DNA. (Invitrogen, CA) in PCR using following primers:

5'-GCGC<u>ACTAGT</u>AAAATGAACGACCAAACGCAATTTACAGAAAGGGCTCTA-3' [SEQ ID NO: 40]

5'-GCGC<u>ACTAGT</u>TAATCTAGGTCATCATCAATTTCCATACTGTCCTCA-3' [SEQ ID NO: 41]

SpeI restriction endonuclease sites (underlined) are provided in both primers. The amplified PCR product is digested at the ends with SpeI restriction endonuclease and inserted into XbaI site of the pVL1393 vector to yield a polyhedrin transfer vector designated pVL-104 (FIG. 9). Orientation of the Hsp104 gene is established by restriction analysis with BglII, or EagI or EcoRV restriction endonucleases and confirmed by the DNA sequencing.

In another embodiment, yeast Saccharomyces cerevisiae Hsp104 is amplified from yeast genomic DNA (Invitrogen, CA) in PCR using following primers:

5'-GCGC<u>CCCGGG</u>AAAATGAACGACCAAACGCAATTTACAGAAAGGGCTCTA-3' [SEQ ID NO: 42]

5'-GCGC<u>CCCGGG</u>TTAATCTAGGTCATCATCAATTTCCATACTGTCCTCA-3' [SEQ ID NO: 43]

XmaI restriction endonuclease sites (underlined) are provided in both primers. The amplified PCR product is digested at the ends with XmaI restriction endonuclease and inserted into XmaI site of the AB3-Hop-90 vector to yield AB3-104-Hop-90 plasmid transfer vector (FIG. 8). Orientation of the Hsp104 gene is established by restriction analysis with BglII or EcoRV restriction endonucleases and confirmed by the DNA sequencing.

cDNA encoding calnexin is amplified in PCR using following primers:

5'-GCGC<u>GGATCC</u>TAGAGATCATGGAAGGGAAGTGGT-3' [SEQ ID NO: 44]

5'-GCGC<u>GGATCC</u>GTTTCACTCTCTTCGTGGCTTTCTGT-3' [SEQ ID NO: 45]

Figure 10:
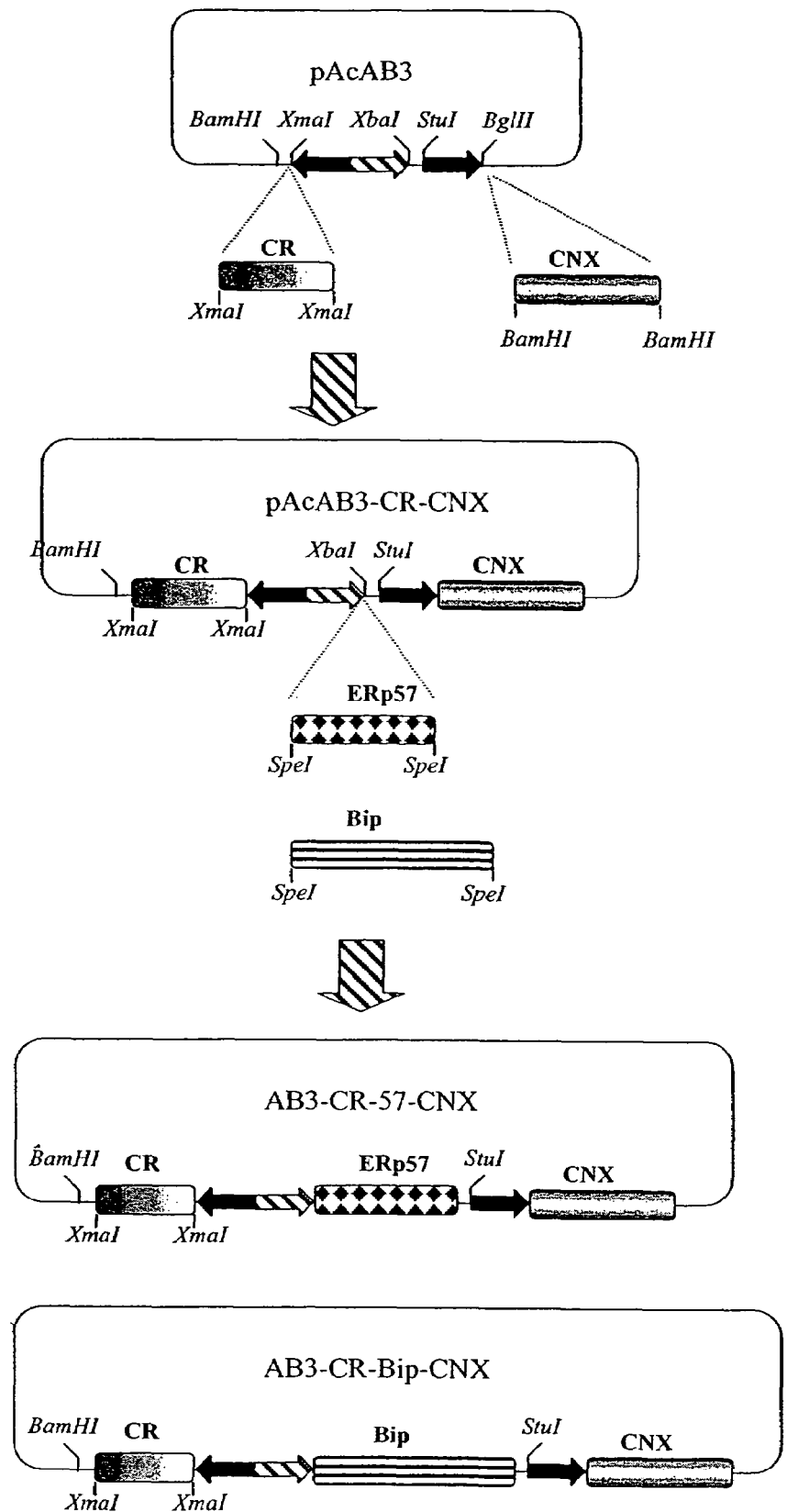
FIG. 10 shows the construction of two CR-CNX-containing expression vectors including: the AB3-CR-57-CNX construct that expresses CR, CNX and ERp57 and the AB3-CR-Bip-CNX construct that expresses calreticulin, calnexin and Bip.

BamHI restriction endonuclease site (underlined) is provided in both primers. The amplified PCR product is digested at the ends with BamHI restriction endonuclease and inserted into BamHI site of the pVL1393 vector to yield a polyhedrin transfer vector designated pVL-CNX (FIG. 9). Orientation of the calnexin gene is established by restriction analysis with HindIII restriction endonuclease and confirmed by the DNA sequencing. The same PCR fragment is also inserted into BglII site of the pAcAB3 vector to yield AB3-CNX plasmid transfer vector (FIG. 10).

Alternatively, cDNA encoding VIPL is amplified using primers SEQ ID NO: 38 and 39, digested with BamHI and inserted into the BglII site of the pAcAB3 vector to yield AB3-VIPL plasmid transfer vector, which is used for subsequent manipulations as described below for AB3-CNX plasmid transfer vector FIG. 10).

Next, cDNA encoding calreticulin is amplified in PCR using following primers:

5'-GCGC<u>AGATCT</u>GCCATGCTGCTATCCGTGCCGCT-3' [SEQ ID NO: 49]

5'-CGCG<u>AGATCT</u>GCCTCTCTACAGCTCGTCCTTG-3' [SEQ ID NO: 46]

BglII restriction endonuclease sites (underlined) are provided in both primers. The amplified PCR product is digested at the ends with BglII restriction endonuclease and inserted into BamHI site of the pVL1393 vector to yield a polyhedrin transfer vector designated pVL-CNX. Orientation of the calreticulin gene is established by restriction analysis with double digestion with HindIII and BamHI restriction endonuclease and confirmed by the DNA sequencing. The same PCR fragment is also inserted into BamHI site of the AB3-CNX vector to yield AB3-CR-CNX plasmid transfer vector.

cDNA encoding ERp57 is amplified in PCR using primers SEQ ID NO: 26 and 27, which were described above. SpeI restriction endonuclease sites (underlined) are provided in both primers. The amplified PCR product is digested with SpeI restriction endonuclease and inserted into the pVL1393 vector digested with XbaI restriction endonuclease to yield a polyhedrin transfer vector designated pVL-57 (FIG. 9). Orientation of the ERp57 gene is established by analysis with PstI restriction endonuclease and confirmed by the DNA sequencing.

The same PCR fragment is also inserted into XbaI site of the AB3-CR-CNX vector to yield AB3-CR-ERp57-CNX plasmid transfer vector (FIG. 10). Orientation of the ERp57 gene is established by restriction analysis with PstI and XmaI restriction endonucleases and confirmed by the DNA sequencing.

cDNA encoding Bip is amplified in PCR using primers SEQ ID NO: 20 and 21.

SpeI restriction endonuclease sites are provided in both primers. The amplified PCR product is digested with SpeI restriction endonuclease and inserted into the pVLI 393 vector digested with XbaI restriction endonuclease to yield a polyhedrin transfer vector designated pVL-Bip (FIG. 9). Orientation of the Bip gene is established by analysis with EcoRI restriction endonuclease and confirmed by the DNA sequencing.

The same PCR fragment is also inserted into XbaI site of the AB3-CR-CNX vector to yield AB3-CR-Bip-CNX plasmid transfer vector (FIG. 10). Orientation of the Bip gene is established by restriction analysis with EcoRI and XmaI restriction endonucleases and confirmed by the DNA sequencing.

cDNA encoding Hsp90 is amplified in PCR using following set of primers:

5'-GCGC<u>ACTAGT</u>AAAATGCCTGAGGAAGTGCACCA-3' [SEQ ID NO: 47]

5'-GCGC<u>ACTAGT</u>AATCGACTTCTTCCATGCGAGA-3' [SEQ ID NO: 48]

SpeI restriction endonuclease sites are provided in both primers. The amplified PCR product is digested with SpeI restriction endonuclease and inserted into the pVL1393 vector digested with XbaI restriction endonuclease to yield a polyhedrin transfer vector designated pVL-90 (FIG. 9). Orientation of the Hsp90 gene is established by restriction analysis with EcoRI restriction endonuclease and confirmed by the DNA sequencing.

BacPAK6 or BacPAK6-PDI DNA is digested with Bsu36.I restriction endonuclease and co-transfected with generated in this example polyhedrin transfer vector DNA carrying polynucleotide sequences encoding molecular chaperones. Recombinant helper baculoviruses are selected, plaque purified and characterized as described (Kitts P. et al., Biotechniques, 14: 810–817, 1993). For convenience, generated helper viruses are designated H, followed by abbreviation of molecular chaperones as in the corresponding transfer vectors. For instance, helper virus generated in co-transfection of BacPAK6 and pVL-104 plasmid transfer vector is designated H104, and generated in co-transfection of BacPAK6-PDI and the same plasmid is designated H104-PDI.

In another embodiment G-70-40* recombinant baculovirus DNA is digested with Bsu36.1 and co-transfected with generated in this example polyhedrin transfer vector DNA carrying polynucleotide sequences encoding molecular chaperones. Recombinant helper baculoviruses are selected, plaque purified and characterized as described (Kitts P. et al., Biotechniques, 14: 810–817, 1993).

The generated viruses are designated as explained above, for example helper virus generated in co-transfection of G-70-40* and AB3-23-Hop-90 plasmid transfer vector is designated H-G-70-40-23-Hop-90, and generated in co-transfection of BacPAK6-PDI and the same plasmid is designated H-G-23-Hop-90-PDI.

In still another embodiment G-Bip-CR recombinant baculovirus DNA is digested with Bsu36.I and co-transfected with generated in this example polyhedrin transfer vector DNA carrying polynucleotide sequences encoding molecular chaperones. Recombinant helper baculoviruses are selected, plaque purified and characterized as described (Kitts P. et al., Biotechniques, 14: 810–817, 1993).

The generated viruses are designated as explained above, for example helper virus generated in co-transfection of G-Bip-HEDJ and AB3-CR-57-VIPL plasmid transfer vector is designated H-G-Bip-HEDJ-CR-57-VIPL.

Example 10

Effect of Molecular Chaperones on Protein Solubility

Six proteins, i.e. yeast and mouse terminal amidase, Acc#Q64311 and Acc#P40354; *Arabidopsis thaliana* myrcene/ocymeme synthase, acc# NM_127982; *Arabidopsis thaliana* monoterpene synthase/cyclase family, acc#NM_117775; Clarka brewery S-adenosyl-L-methionine: salicylic acid carboxyl methyltransferase, acc#AAF00108; *Arabidopsis thaliana* methyltransferase-related protein, acc#NM_148466; were previously demonstrated to be completely insoluble when expressed using *E. coli* vectors. The genes encoding these proteins are amplified in PCR and cloned into pAcGHLT polyhedrin plasmid transfer vectors (Pharmingen, La Jolla, Calif.) in frame with polynucleotide sequence encoding 6×His tag. The plasmid transfer vectors with the inserted genes were kindly provided by Dr. Joseph Noel, Salk Institute, La Jolla, Calif. Each plasmid transfer vector DNA is co-transfected with baculovirus vector DNA linearized with Bsu.36.I restriction endonuclease and the recombinants were selected as described (Kitts P. et al., Biotechniques, 14: 810–817, 1993). Parental baculovirus vectiors DNA BacPAK6 as well as baculovirus vector DNA G-70-40 and G-70-40*, which provide for expression of Hsc70 and Hsp40 molecular chaperones were used. The resulting viruses were designated according with their accession numbers and the baculovirus vectors:

G-70-40-Q6431, G-70-40-P40354, G-70-40-NM_127982, G-70-40-NM_117775, G-70-40-AAF00108, G-70-40-NM_148466,

G-70-40*-Q6431, G-70-40*-P40354, G-70-40*-NM_127982, G-70-40*-NM_117775, G-70-40*-AAF00108, G-70-40*-NM_148466,

BacPAK6-Q6431, BacPAK6-P40354, BacPAK6-NM_127982, BacPAK6-NM_117775, BacPAK6-AAF00108, BacPAK6-NM_148466.

About 90% confluent monolayers of Sf9 cells are infected with the recombinant baculoviruses at multiplicity 5 p.f.u/cell, incubated at 27 degrees C. and harvested at 60 hours post infection. Cells are washed with phosphate buffered saline (PBS) and lysed in TNN buffer (50 mM Tris-HCl pH 8.0, 150 mM NaCl, 0.5% "NONIDET-P40").

The cell lysates are subject to centrifugation in a microfuge at 14,000 rpm for 15 minutes. Pellets (containing insoluble proteins) and supernatants (containing soluble proteins), together with a negative control baculovirus-infected cell lysate, which does not contain foreign proteins, are separated by sodium dodecyl sulfate polyacrylamide gel electrophoresis (SDS-PAGE). The expressed recombinant HGV proteins are identified as additional bands on the gel stained with Coomassie blue as compared with the negative control lane.

In all cases, G-70-40* vector provided about the same level of expression of a protein of interest as the parental BacPAK6 vector, however the expression level was only about 60% of that with the G-70-40 vector.

One of the expressed proteins, yeast terminal amidase, was predominantly soluble when expressed using BacPAK6 vector without molecular chaperones, which is probably due to more adequate insect cell protein folding machinery regarding folding eucaryotic proteins.

Another protein, Clarka brewery S-adenosyl-L-methionine: salicylic acid carboxyl methyltransferase was predominantly soluble when expressed using G-70-40 or G-70-40* vector with molecular chaperones, however it was predominantly insoluble when expressed using BacPAK6 vector without molecular chaperones.

Remaining four proteins were predominantly insoluble when expressed using any of the vectors. However, the protein aggregates, which were obtained using vectors providing molecular chaperones G-70-40 or G-70-40* had very different properties from the protein aggregates obtained using a vector BacPAK6, which does not provide chaperones. The protein aggregates obtained using vectors providing Hsc70 and Hsp40 chaperones incorporated large amounts of these chaperones and were much more easily solubilized, than the protein aggregates obtained using the vector without molecular chaperones.

Aggregates of these four proteins obtained with overexpression of Hsc70 and Hsp40 molecular chaperones were nearly completely solubilized in 3M urea 0.1 M carbonate buffer pH 9.5 during 15 min incubation at room temperature, whereas aggregates of the same proteins remained largely insoluble at the same conditions. It is likely that more sparing conditions can be worked out for co-aggregates of these proteins with molecular chaperones. For example, one of these proteins, *Arabidopsis thaliana* methyltransferase-related protein, was nearly completely solubilized in the same buffer without urea, when it was expressed with the molecular chaperones, and remained aggregated if it was expressed without the chaperones.

Importantly, protein aggregates consisting largely of correctly folded protein, have the same advantage of fast protein semi-purification and protection from proteases as typical inclusion bodies. The protein aggregates were routinely purified to about 60–80% or more purity using the same protocol as was applied for the inclusion bodies formed without additional molecular chaperones.

Cells are washed with PBS and lysed in TNN buffer, and soluble and insoluble fractions are separated by centrifugation in a microfuge at 14,000 rpm for 15 min. The insoluble pellet is washed with 0.2 M sodium phosphate pH 8.0–150 mM NaCl. The pellet is then sonicated for 5 min in a Branson Sonier 450 sonicater set at output 6 at a 20 sec cycle for 5 min (so as not to causing excessive foaming or heating of the sample). The sonicated mixture is again subject to centrifugation in a microfuge at 14,000 rpm for 15 min. The obtained insoluble fraction contained about 60–90% pure protein of interest depending on the level of protein expression, with the purity of preparation correlating with the level of protein expression. The yield of the protein of interest obtained by purification of protein aggregates produced using G-70-40* vector or inclusion bodies produced using BacPAK6 vector was about the same. The purity of the protein in these semi-purified preparations was also similar, albeit a little reduced in the protein aggregates produced using G-70-40* vector as these protein aggregates contain substantial amount of Hsc70 and Hsp40 molecular chaperones.

The solubilized protein aggregates are brought into the media compatible with their biological activity using methods known to those skilled in the art (Randolph T. W., et al., U.S. Pat. No. 6,489,450, 2002), incorporated herein by reference. Biological activity, for example enzymatic activity of proteins obtained with molecular chaperones is tested. Yield of a biologically active protein obtained without chaperones is typically inferior to the yield of biologically active protein with the chaperones, as protein aggregates, which are formed in the presence of large amount of molecular chaperones contain better folded protein than the aggregates formed without additional chaperones.

Thus, it is demonstrated that in every investigated case of an insoluble protein, its solubility was improved at some conditions or another when compared to the same protein expressed without molecular chaperones.

Further improvement in solubility of these proteins is achieved either by co-expressing them in their native environment with chaperones belonging to that environment, or by providing additional cytoplasmic molecular chaperones, Hsp90 and Hop are preferred, and Hsp90, Hop and p23 are more preferred. These additional chaperones are provided in co-infection with helper viruses H-Hop-90 or H-23-Hop-90 as described in EXAMPLE 10. Alternatively, a baculovirus vector DNA providing Hsc70, Hsp40, Hsp90, Hop in the same genome can be constructed.

Example 11

Co-Infections with Helper Viruses

Co-infection with helper viruses expressing molecular chaperones is employed when there is a room for improvement in folding of a protein of interest expressed using virus vectors, which provide or do not provide molecular chaperones. Though it is always preferable to express all molecular chaperones in the same genome with a protein of interest, helper viruses provide a useful flexible tool when such vectors are not available. They can be also applied when the recombinant baculovirus was already constructed using extant vectors, though better results are achieved if that protein of interest is expressed using the vectors of this invention providing molecular chaperones.

Helper viruses described in EXAMPLE 9 are used to provide molecular chaperones into the cells infected with recombinant baculoviruses expressing a protein of interest, with or without molecular chaperones. Co-infections can easily be performed by those of skill in the art (King L. A. and Possee R. D., The baculovirus expression system. A laboratory guide, Chapman & Hall, London, New York, Tokyo, Melbourne, Madras, 1992). By way of example, co-infection experiments may be performed as is described below for the co-infection of a helper virus H-23-Hop-90 and a recombinant baculovirus expressing proteins of interest, i.e. G-70-40*-P40354, G-70-40*-NM_127982, G-70-40*-NM_117775, G-70-40*-NM_148466. The ratio between the helper virus and the virus expressing a protein of interest can be selected based on the level of protein expression of the major interacting molecular chaperons in a helper virus and a virus expressing a protein of interest and the available data on the ratio of major chaperones (Murphy, P. J. M. et al., J. Biol. Chem., 276: 30092–30098, 2001). The ratio between a helper virus and a virus expressing a protein of interest can be optimized by decreasing or increasing the m.o.i. ratio between these viruses, and choosing the ratio resulting in the best yield of soluble protein. Multiplicity of infection of 5 or more for each type of virus participating in co-infection is preferred to facilitate more simultaneous infection of the cells with all types of viruses. A range of the ratios, for example 1:3, 1:1, 3:1, is initially tried. Next, a more narrow range of ratios can be tried if further optimization is desired.

Semi-confluent monolayers of Sf21 cells are grown in 150 square cm tissue culture flasks in IC-100 medium (King L. A. and Possee R. D., The baculovirus expression system. A laboratory guide, Chapman & Hall, London, New York, Tokyo, Melbourne, Madras, 1992) and supplemented with 10% fetal calf serum (FCS) (Gemini, Calabasas, Calif.). The medium is discarded and monolayers are either: (a) co-infected with the helper virus H23-Hop-90 at multiplicities 5, 15, 45 and with a recombinant baculovirus expressing a protein of interest, for example G-70-40*-P40354 or G-70-40*-NM_127982 or G-70-40*-NM_117775 or G-70-40*-NM_148466 at (m.o.i.) 5 each; (b) with a recombinant baculovirus expressing a protein of interest, for example G-70-40*-P40354 or G-70-40*-NM_127982 or G-70-40*-NM_1117775 or G-70-40*-NM_148466 at (m.o.i.) 5 each. Adsorbsion of viruses was allowed to proceed at room temperature for 1 h on a slow rocker. 30 ml of fresh TC-100/10% FCS is added to the tissue culture flask and incubation continues at 27 degrees C. At 60 hours post-infection, monolayers were washed with PBS and lysed with TNN buffer, soluble and insoluble fractions are separated and compared for the yield of proteins of interest according to the method of EXAMPLE 10. Improvement in protein solubility due to application of molecular chaperones using a helper virus is observed as increased concentration of protein in soluble versus insoluble fraction. In cases when majority of the protein still remains insoluble, improvement in protein solubility is observed as using less aggressive conditions for solubilization of protein aggregates observed with molecular chaperones provided via helper virus versus solubilization of protein aggregates observed without these chaperones. Less aggressive conditions means reduced concentration of a chaotropic agent, closer to neutral pH, substituting for a detergent, which is more compatible with the protein biological activity, etc. For example, if the protein aggregates obtained without a helper virus require 3 M urea-pH 9.5 for their solubilization, protein aggregates obtained with a helper virus may not require urea, or require 1 or 2 M urea, or could be solubilized at more neutral pH, for example pH 8, 8.5 or 9 with or without 1,2, 3 M urea.

Furthermore, solubilized protein aggregates are brought into the media compatible with their biological activity using methods known to those skilled in the art (Randolph T. W., et al., U.S. Pat. No. 6,489,450, 2002), incorporated herein by reference. Biological activity, for example enzymatic activity of proteins obtained with molecular chaperones is tested. Yield of a biologically active protein obtained without chaperones is typically inferior to the yield of biologically active protein with the chaperones, as protein aggregates, which are formed in the presence of large amount of molecular chaperones contain better folded protein than the aggregates formed without additional chaperones.

Example 12

Transfer Vectors Providing Insect Signal Sequences

Typically, proteins, which are translocated across the membrane of the endoplasmic reticulum, contain N-terminal hydrophobic signal peptide, which facilitates this translocation. Foreign signal sequences can function in a distant host, for example a signal sequence of a mammalian protein can be active in insect cells. It could be effective in facilitating translocation of said protein, its native folding and could result in production of the required amount of a biologically protein.

However, this approach may work below-expectation if a foreign signal sequence fails to facilitate translocation of the bulk of the produced foreign protein through the endoplasmic reticulum membrane. In this case a protein of interest will remain in the cytoplasm and can be misfolded and degraded. This is because cytoplasm differs from the endoplasmic reticulum in the oxidizing environment and sets of molecular chaperones required for the formation of disulfide bonds and folding of the translocated proteins. Some protein modifications, which may be required for correct protein folding and its biological activity, for example glycosylation, are also provided only in the endoplasmic reticulum.

Even if the protein translocation occurs, foreign signal signal sequence may not be cleaved efficiently, thus anchoring the polyprotein chain to the membrane and hindering its interaction with molecular chaperones and protein modifying enzymes.

In such cases, utilization of an insect cell signal sequences in N-terminal fusion with the protein of interest is preferred. However, insect signal sequences are not equivalent in the ability to translocate proteins. Some of the translocated proteins of the insect cells may not require highly efficient translocation if they are produced slowly and to a low level by the insect cells. Therefore, insect signal sequences, which are capable of fast translocation of large amount of protein are preferred. While not limiting the choice of the signal sequences, examples of such sequences comprise signal sequences of arthropod silk proteins and poison proteins, such as *Antheraea* mylitta fybroin heavy chain, acc#AY136274 and Pimpla hypochondriaca cystein-rich venom protein 6, acc#AJ438997.

Figure 11:
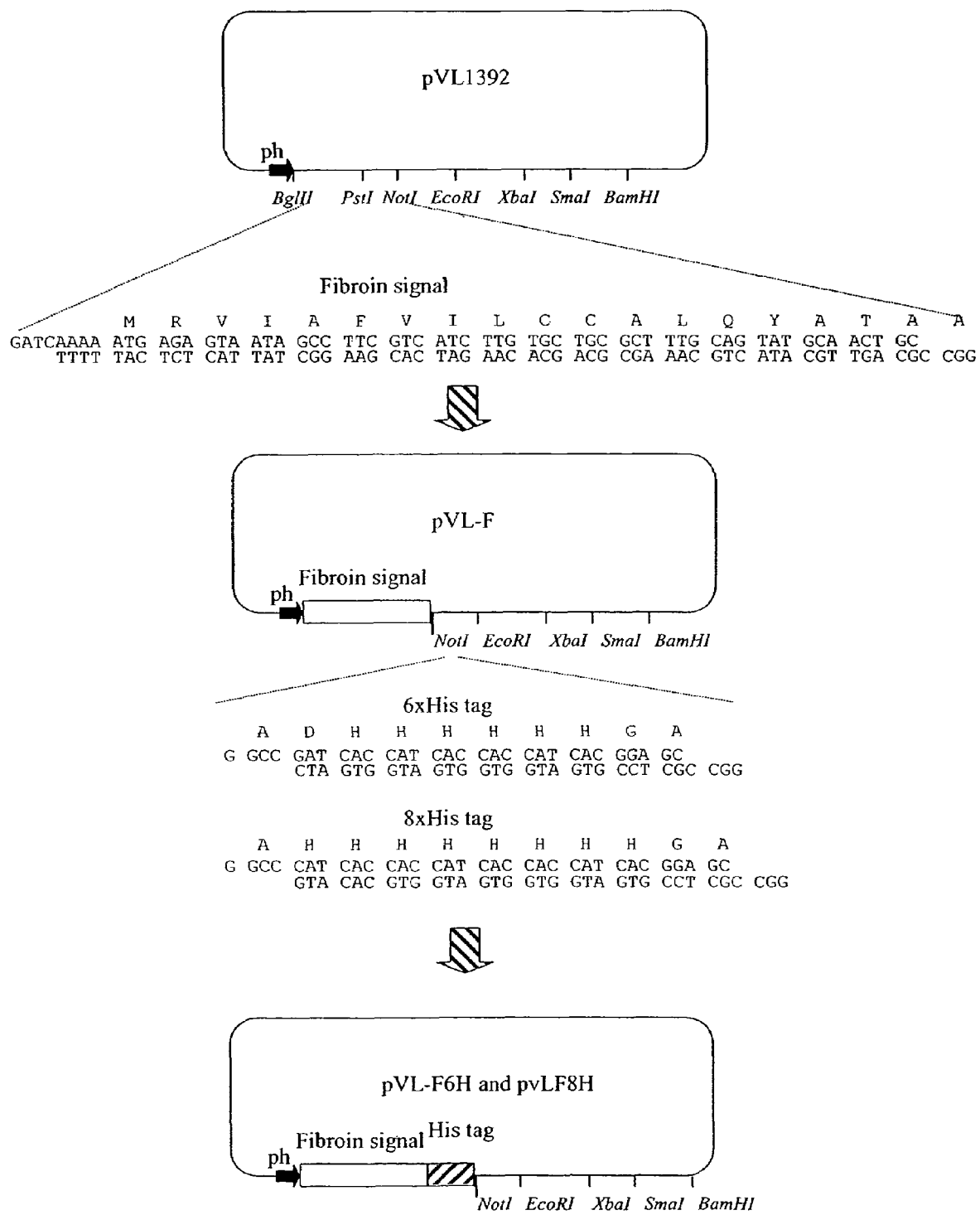
FIG. 11 shows the construction of polyhedrin transfer vectors pVL-F6H and pVL-F8H.
Figure 12:
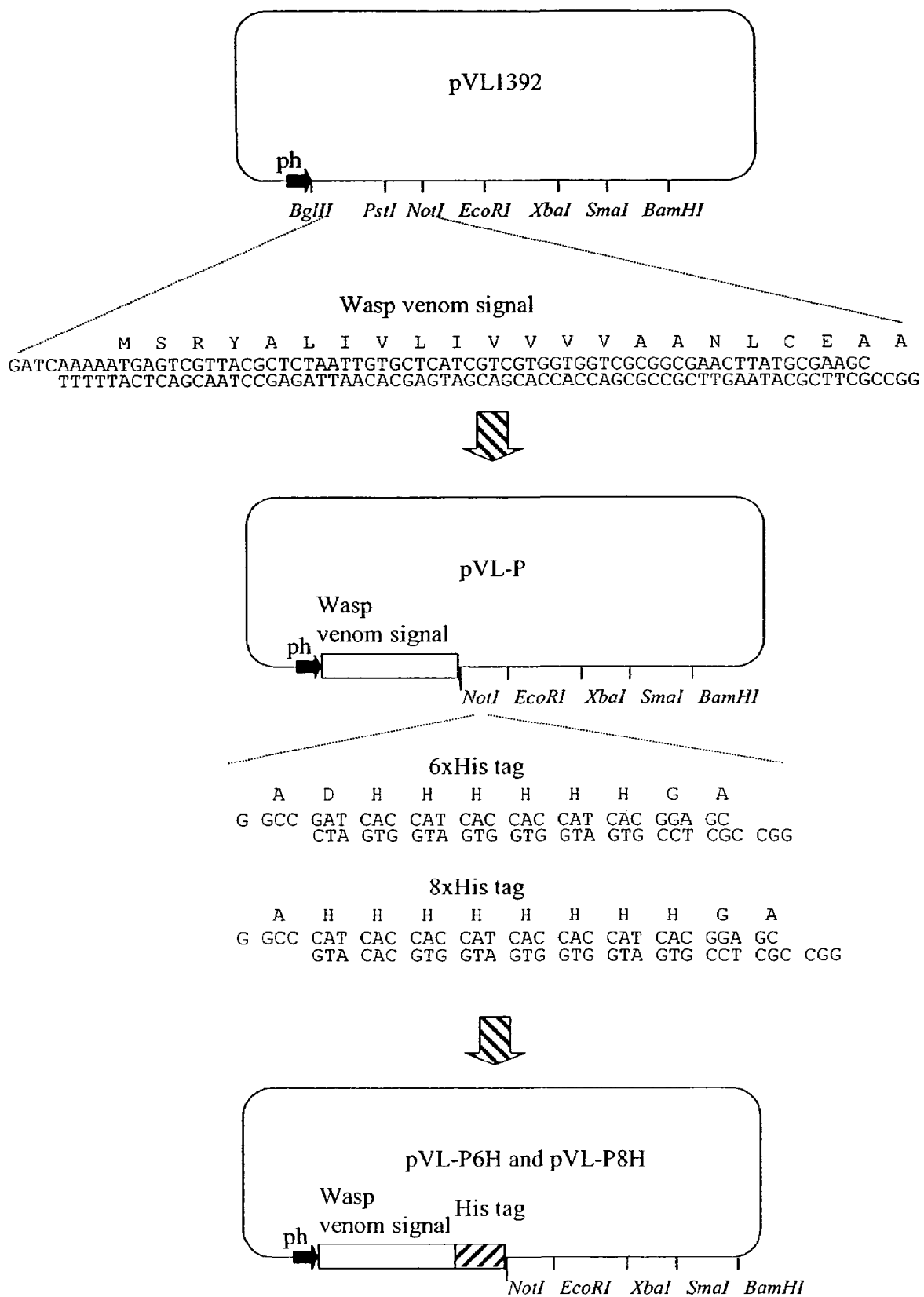
FIG. 12 shows the construction of polyhedrin transfer vectors pVL-P6H and pVL-P8H.

Construction of polyhedrin transfer vectors providing these sequences is represented on FIGS. 11 and 12.

Oligonucleotides encoding *Antheraea* mylitta fybroin heavy chain signal peptide amino acid sequence MRVI-AFVILCCALQYAT, residues 1 through 17 of SEQ ID NO:50, are annealed and cloned into polyhedrin transfer vector pVL1392 digested with BglII and NotI restriction endonucleases to yield pVL-F vector (FIG. 11). The insertion of the oligonucleotide sequence is confirmed by DNA sequencing. A foreign gene of interest can be conveniently inserted in lieu of the polyhedrin promoter and in frame with the *Antheraea mylitta* fybroin heavy chain signal sequence using NotI, EcoRI, XbaI, SmaI, BamHI unique cloning site. Cleavage of the signal peptide can occur within the QYATAA, residues 14 through 19 of SEQ ID NO:50, sequence provided at the end of the signal sequence.

Since chelate chromatography affinity purification of a protein of interest is often desirable, a 6×His tag, residues 3 through 8 of SEQ ID NO:53, or 8×His tag, residues 2 through 9 of SEQ ID NO:56, is provided in lieu of the signal peptide cleavage signal. To this end, a double-stranded oligonucleotide is inserted into the NotI site of the pVL-F vector to generate pVL-F6H and pVL-F8H vectors (FIG. 11).

In another embodiment, oligonucleotides encoding Pimpla hypochondriaca cystein-rich venom protein 6 signal peptide amino acid sequence MSRYALIVLIVVVAANL-CEA, residues 1 through 21 of SEQ ID NO:59, are annealed and cloned into polyhedrin transfer vector pVL1392 digested with BglII and NotI restriction endonucleases to yield pVL-W vector (FIG. 12). The insertion of the oligonucleotide sequence is confirmed by DNA sequencing. A foreign gene of interest can be conveniently inserted in lieu of the polyhedrin promoter and in frame with the *Antheraea mylitta* fybroin heavy chain signal sequence using NotI, EcoRI, XbaI, SmaI, BamHI unique cloning site. Cleavage of the signal peptide can occur within the CEAA, residues 19 through 22 of SEQ ID NO:59, sequence provided at the end of the signal peptide sequence.

Since chelate chromatography affinity purification of a protein of interest is often desirable, a 6×His tag or 8×His tag is provided in lieu of the signal peptide cleavage signal. To this end, a double-stranded oligonucleotide is inserted into the NotI site of the pVL-P vector to generate pVL-P6H and pVL-P8H vectors (FIG. 12).

Genes encoding proteins of interest are cloned into pVL-F, pVL-P, pVL-F6H, pVL-F8H, pVL-P6H or pVL-P8H vectors in-frame with the signal peptide sequences and are co-transformed with any of the linearized derivatives of the BacPAK6 DNA as described (Kitts). Use of these vectors with the BacPAK6 derivatives overproducing endoplasmic reticulum molecular chaperones, such as G-BIP-CR, G-57-CR, G-PPI-CR, G-CR, G-BIP, G-BIP-ERdj5, G-BIP-HEDJ and helper viruses H-ERp57-PDI, H-Ero1, H-HEDJ, H-CR, H-CNX, H-VIPL, H-CR-ERp57-CNX, H-CR-ERp57-CNX, H-CR-BIP-CNX is preferred. However, use of these signal sequences is not limited to these or other BacPAK6 derivatives, as the sequences can be easily transferred into other vectors compatible with other vector systems, for example Bac-to-Bac, Bac-N-Blue and BaculoDirect vector DNA available from Invitrogen, Carlsbad, Calif.

What is claimed is:

1. An isolated recombinant baculovirus vector comprising polynucleotides encoding at least two molecular chaperones and a foreign polynucleotide sequence of interest, wherein the polynucleotides are expressed from one or more cassettes within the recombinant vector, and wherein polynucleotides encoding the chaperones and the foreign polynucleotide sequence of interest are separated by at least 1000 nucleotides.

2. The recombinant vector of claim 1 wherein the foreign polynucleotide sequence of interest allows convenient insertion of another polynucleotide sequence of interest and selection for vectors with the inserted foreign polynucleotide sequence encoding any protein of interest.

3. The recombinant vector of claim 1 wherein the foreign polynucleotide sequence of interest encodes a reporter protein allowing for convenient negative selection of recombinant vectors expressing any protein of interest.

4. The recombinant vector of claim 1 wherein said foreign polynucleotide sequence of interest encodes beta-galactosidase.

5. The recombinant vector of claim 1 wherein the foreign polynucleotide sequence of interest encodes a foreign protein of interest.

6. The recombinant vector of claim 1 wherein the molecular chaperones are selected from the group consisting of Hsp70, comprising prokaryotic DnaK, Hsc66 (HscA), and Hsc62 and eucaryotic Hsp72, Hsp73, Hsc70, Prp73, Bip (Grp78), Stch, mt-Hsp70 (Grp75, Pbp74), Ssal-4p, Ssbl, 2p, Ssdlp (Kar2p), Ssi1p (Lhs1p), mt-Hsc70 (Ssc1p), Ssh1p (Ssq1p), and Ss2p (Ssj1p), and Hsp40 (DnaJ) comprising prokaryotic DnaJ, CbpA, Hsc20 (HscB), Dj 1A(RscG) and eukaryotic Hdj1 (Hsp40), Hdj2 (HSDJ), Hsj1 a/b neurone specific, HLJ1, Zuotin, Sis1p, Ydj1p (Mas5p), Dj1p, Caj1, Scj1p, Sec63p(Npl1p), Jem1p, Mdj1p, Jac1p, Tim44, Mdj2p, cysteine-string protein ALA-D, Mtj1 (Sec63p-like), h-Tid-1S, h-Tid-1L, and mTim-44.

7. The recombinant vector of claim 1 wherein at least one molecular chaperone is an Hsp70 molecular chaperone.

8. The recombinant vector of claim 1 wherein at least one molecular chaperone is an Hsp70 molecular chaperone and another is a molecular chaperone having a DNAJ domain.

9. The recombinant vector of claim 1 wherein one molecular chaperone is an Hsp70 and another is an Hsp40 molecular chaperone.

10. The recombinant vector of claim 1 having polynucleotides encoding at least one molecular chaperone inserted into an intergenic region or non-essential gene.

11. The recombinant vector of claim 1 wherein a site for insertion of a gene encoding a protein of interest or molecular chaperone contains a unique restriction endonuclease site comprising six or more nucleotides for specific recognition by a restriction endonuclease.

12. The recombinant vector of claim 1 wherein the vector sequence or the genes encoding molecular chaperones are mutated in order to allow unique cleavage of the vector at the site intended to insert a protein of interest or a chaperone.

13. The recombinant vector of claim 1 having a polynucleotide sequence of interest inserted into a polyhedrin site and a polynucleotide sequence encoding for at least one molecular chaperone inserted into a non-polyhedrin site.

14. The recombinant baculovirus vector of claim 13, wherein said non-polyhedrin site is either an intergenic region or a non-essential gene.

15. The recombinant baculovirus vector of claim 13 wherein said non-polyhedrin site is ecdysteroid UDP-glycosyltransferase (EGT).

16. The recombinant baculovirus vector of claim 15 wherein the chaperone is protein disulfide isomerase (PDI) and wherein the PDI is inserted into a 10 site.

17. The recombinant vector of claim 7 wherein the foreign polynucleotide sequence of interest is thrombopoietin.

18. A method for producing a foreign protein comprising the steps of:
  a. introducing the recombinant vector of claim 1 into insect host cells;
  b. culturing the insect host cells harboring the recombinant vector of claim 1 under conditions which allow expression of said foreign protein and said molecular chaperones at levels suitable for stabilization and/or solubilization of the foreign protein; and c. isolating said foreign protein from the culture.

19. The method of claim 18 wherein in addition to the vector of claim 1, one or more vectors are introduced into appropriate insect host cells, wherein the additional vectors encode one or more molecular chaperone(s) selected from the group consisting of Hsp70, comprising prokaryotic DnaK, Hsc66 (HscA), and Hsc62 and eucaryotic Hsp72, Hsp73, Hsc70, Prp73, Bip (Grp78), Stch, mt-Hsp70 (Grp75, Pbp74), Ssal-4p, Ssbl, 2p, Ssdlp (Kar2p), Ssi1p (Lhs1p), mt-Hsc70 (Ssc1p), Ssh1p (Ssq1p), and Ss2p (Ssj1p), and Hsp40 (DnaJ) comprising prokaryotic DnaJ, CbpA, Hsc20 (HscB), Dj 1A(RscG) and eukaryotic Hdj1 (Hsp40), Hdj2 (HSDJ), Hsj1 a/b neurone specific, HLJ1, Zuotin, Sis1p, Ydj1p (Mas5p), Dj1 p, Caj1, Scj1p, Sec63p(Npl1p), Jem1p, Mdj1p, Jac1p, Tim44, Mdj2p, cysteine-string protein ALA-D, Mtj1 (Sec63p-like), h-Tid-1S, h-Tid-1L, and mTim-44.

20. The method of claim 18 wherein the foreign polynucleotide sequence of interest is operably linked to a polynucleotide sequence encoding an insect or baculovirus signal peptide selected from the group consisting of silk fibroin coding sequence, wasp *Pimpla hypochondriaca* cysteine-rich venom protein coding sequence, Baculovirus ecdysteroid UDP-glycosyltransferase (EGT) coding sequence and Honeybee melittin coding sequence.

* * * * *

SEQUENCE LISTING

<160> NUMBER OF SEQ ID NOS: 61

<210> SEQ ID NO 1
<211> LENGTH: 30
<212> TYPE: DNA
<213> ORGANISM: Artificial sequence
<220> FEATURE:
<223> OTHER INFORMATION: Primer

<400> SEQUENCE: 1
gcgcaagctt gcagcatgtt aagtttggcg                30

<210> SEQ ID NO 2
<211> LENGTH: 24
<212> TYPE: DNA
<213> ORGANISM: Artificial sequence
<220> FEATURE:
<223> OTHER INFORMATION: Primer

<400> SEQUENCE: 2
atcatgggca gacacaccat gggt                24

<210> SEQ ID NO 3
<211> LENGTH: 30
<212> TYPE: DNA
<213> ORGANISM: Artificial sequence
<220> FEATURE:
<223> OTHER INFORMATION: Primer

<400> SEQUENCE: 3
gcgcacctag gttgctgatg atccagcatg                30

<210> SEQ ID NO 4
<211> LENGTH: 36
<212> TYPE: DNA
<213> ORGANISM: Artificial sequence
<220> FEATURE:
<223> OTHER INFORMATION: Primer

<400> SEQUENCE: 4
cgcgcctagg ctcgagtact aataaccgga tccccg                36

<210> SEQ ID NO 5
<211> LENGTH: 44
<212> TYPE: DNA
<213> ORGANISM: Artificial sequence
<220> FEATURE:
<223> OTHER INFORMATION: Primer

<400> SEQUENCE: 5
gcgcggatcc aaaaaatgag taaaggagaa gaacttttca ctgg                44

<210> SEQ ID NO 6
<211> LENGTH: 38
<212> TYPE: DNA
<213> ORGANISM: Artificial sequence
<220> FEATURE:
<223> OTHER INFORMATION: Primer

<400> SEQUENCE: 6
gcgcggatcc tctttgtata gttcatccat gccatgtg                38

<210> SEQ ID NO 7
<211> LENGTH: 37
<212> TYPE: DNA

```
<213> ORGANISM: Artificial sequence
<220> FEATURE:
<223> OTHER INFORMATION: Primer

<400> SEQUENCE: 7
cgcgcactag tagaagatgg tgaaagaaac aacttac                              37

<210> SEQ ID NO 8
<211> LENGTH: 34
<212> TYPE: DNA
<213> ORGANISM: Artificial sequence
<220> FEATURE:
<223> OTHER INFORMATION: Primer

<400> SEQUENCE: 8
gcgccactag ttaagaggtc tgacactgaa cacc                                 34

<210> SEQ ID NO 9
<211> LENGTH: 47
<212> TYPE: DNA
<213> ORGANISM: Artificial sequence
<220> FEATURE:
<223> OTHER INFORMATION: Primer

<400> SEQUENCE: 9
gcgcactagt acaccccagc aaccatgtcc aagggacctg cagttgg                   47

<210> SEQ ID NO 10
<211> LENGTH: 51
<212> TYPE: DNA
<213> ORGANISM: Artificial sequence
<220> FEATURE:
<223> OTHER INFORMATION: Primer

<400> SEQUENCE: 10
cgcgactagt taatcaacct cttcaatggt gggccccgag gaagcaccac c              51

<210> SEQ ID NO 11
<211> LENGTH: 24
<212> TYPE: DNA
<213> ORGANISM: Artificial sequence
<220> FEATURE:
<223> OTHER INFORMATION: Primer

<400> SEQUENCE: 11
gccaagatca ataccaactg cagg                                            24

<210> SEQ ID NO 12
<211> LENGTH: 42
<212> TYPE: DNA
<213> ORGANISM: Artificial sequence
<220> FEATURE:
<223> OTHER INFORMATION: Primer

<400> SEQUENCE: 12
cgcgctcgag taatttacag tatagtattt taattaatat ac                        42

<210> SEQ ID NO 13
<211> LENGTH: 40
<212> TYPE: DNA
<213> ORGANISM: Artificial sequence
<220> FEATURE:
<223> OTHER INFORMATION: Primer

<400> SEQUENCE: 13
cgcgctcgag cagtatagta ttttaattaa tatacaaatg                           40
```

<210> SEQ ID NO 14
<211> LENGTH: 32
<212> TYPE: DNA
<213> ORGANISM: Artificial sequence
<220> FEATURE:
<223> OTHER INFORMATION: Primer

<400> SEQUENCE: 14
gcgtcccggg ccatgctgct atccgtgccg ct                                32

<210> SEQ ID NO 15
<211> LENGTH: 39
<212> TYPE: DNA
<213> ORGANISM: Artificial sequence
<220> FEATURE:
<223> OTHER INFORMATION: Primer

<400> SEQUENCE: 15
gcgcgcaatg gggcttggag tctgtgggat catcgatct                         39

<210> SEQ ID NO 16
<211> LENGTH: 35
<212> TYPE: DNA
<213> ORGANISM: Artificial sequence
<220> FEATURE:
<223> OTHER INFORMATION: Primer

<400> SEQUENCE: 16
cgcgcaatgc cgaggactgg gacaagcccg agcat                             35

<210> SEQ ID NO 17
<211> LENGTH: 31
<212> TYPE: DNA
<213> ORGANISM: Artificial sequence
<220> FEATURE:
<223> OTHER INFORMATION: Primer

<400> SEQUENCE: 17
cgcgctcgag cctctctaca gctcgtcctt g                                 31

<210> SEQ ID NO 18
<211> LENGTH: 30
<212> TYPE: DNA
<213> ORGANISM: Artificial sequence
<220> FEATURE:
<223> OTHER INFORMATION: Primer

<400> SEQUENCE: 18
gcgcactagt ggatgctgcg cctctccgaa                                   30

<210> SEQ ID NO 19
<211> LENGTH: 30
<212> TYPE: DNA
<213> ORGANISM: Artificial sequence
<220> FEATURE:
<223> OTHER INFORMATION: Primer

<400> SEQUENCE: 19
cgcgaggcct actccttggc gatggcaaag                                   30

<210> SEQ ID NO 20
<211> LENGTH: 46
<212> TYPE: DNA
<213> ORGANISM: Artificial sequence
<220> FEATURE:

-continued

```
<223> OTHER INFORMATION: Primer

<400> SEQUENCE: 20
gcgcactagt caactggctg gcaagatgaa gctctccctg gtggcc          46

<210> SEQ ID NO 21
<211> LENGTH: 39
<212> TYPE: DNA
<213> ORGANISM: Artificial sequence
<220> FEATURE:
<223> OTHER INFORMATION: Primer

<400> SEQUENCE: 21
gcgcactagt ctacaactca tcttttctg ctgtatcct                   39

<210> SEQ ID NO 22
<211> LENGTH: 37
<212> TYPE: DNA
<213> ORGANISM: Artificial sequence
<220> FEATURE:
<223> OTHER INFORMATION: Primer

<400> SEQUENCE: 22
gcgcaggcct gcataagaaa gagaatggga gtctggt                    37

<210> SEQ ID NO 23
<211> LENGTH: 36
<212> TYPE: DNA
<213> ORGANISM: Artificial sequence
<220> FEATURE:
<223> OTHER INFORMATION: Primer

<400> SEQUENCE: 23
gcgctctaga ggtgtcttct gatgtcatct gtcaga                     36

<210> SEQ ID NO 24
<211> LENGTH: 33
<212> TYPE: DNA
<213> ORGANISM: Artificial sequence
<220> FEATURE:
<223> OTHER INFORMATION: Primer

<400> SEQUENCE: 24
gcgcaggcct aaccatggct ccgcagaacc tga                        33

<210> SEQ ID NO 25
<211> LENGTH: 33
<212> TYPE: DNA
<213> ORGANISM: Artificial sequence
<220> FEATURE:
<223> OTHER INFORMATION: Primer

<400> SEQUENCE: 25
gcgcctcgag cactctcaat atccttgcag tcc                        33

<210> SEQ ID NO 26
<211> LENGTH: 39
<212> TYPE: DNA
<213> ORGANISM: Artificial sequence
<220> FEATURE:
<223> OTHER INFORMATION: Primer

<400> SEQUENCE: 26
gcgcactagt aaaatgagac tccgccgcct agcgctgtt                  39
```

<210> SEQ ID NO 27
<211> LENGTH: 34
<212> TYPE: DNA
<213> ORGANISM: Artificial sequence
<220> FEATURE:
<223> OTHER INFORMATION: Primer

<400> SEQUENCE: 27
gcgcactagt gctttagaga tcctcctgtg cctt                34

<210> SEQ ID NO 28
<211> LENGTH: 33
<212> TYPE: DNA
<213> ORGANISM: Artificial sequence
<220> FEATURE:
<223> OTHER INFORMATION: Primer

<400> SEQUENCE: 28
gcgcagatct aaaatgcctg aggaagtgca cca                 33

<210> SEQ ID NO 29
<211> LENGTH: 32
<212> TYPE: DNA
<213> ORGANISM: Artificial sequence
<220> FEATURE:
<223> OTHER INFORMATION: Primer

<400> SEQUENCE: 29
gcgcagatct aatcgacttc ttccatgcga ga                  32

<210> SEQ ID NO 30
<211> LENGTH: 43
<212> TYPE: DNA
<213> ORGANISM: Artificial sequence
<220> FEATURE:
<223> OTHER INFORMATION: Primer

<400> SEQUENCE: 30
gcgcactagt aaaatggagc aggtcaatga gctgaaggag aaa       43

<210> SEQ ID NO 31
<211> LENGTH: 38
<212> TYPE: DNA
<213> ORGANISM: Artificial sequence
<220> FEATURE:
<223> OTHER INFORMATION: Primer

<400> SEQUENCE: 31
gcgcactagt catcaccgaa ttgcaatcag acccagat             38

<210> SEQ ID NO 32
<211> LENGTH: 34
<212> TYPE: DNA
<213> ORGANISM: Artificial sequence
<220> FEATURE:
<223> OTHER INFORMATION: Primer

<400> SEQUENCE: 32
gcgccccggg ttcacaatgg agcctgcttc tgca                 34

<210> SEQ ID NO 33
<211> LENGTH: 35
<212> TYPE: DNA
<213> ORGANISM: Artificial sequence
<220> FEATURE:
<223> OTHER INFORMATION: Primer -continued

```
<400> SEQUENCE: 33
gcgccccggg atattcctta ctccagatct ggcat                              35

<210> SEQ ID NO 34
<211> LENGTH: 50
<212> TYPE: DNA
<213> ORGANISM: Artificial sequence
<220> FEATURE:
<223> OTHER INFORMATION: Primer

<400> SEQUENCE: 34
gcgcactagt gcgcactagt aaaatgggcc gcggctgggg attcttgttt              50

<210> SEQ ID NO 35
<211> LENGTH: 41
<212> TYPE: DNA
<213> ORGANISM: Artificial sequence
<220> FEATURE:
<223> OTHER INFORMATION: Primer

<400> SEQUENCE: 35
gcgcactagt taatgaatat tctgtaacaa gttcctgaag t                       41

<210> SEQ ID NO 36
<211> LENGTH: 33
<212> TYPE: DNA
<213> ORGANISM: Artificial sequence
<220> FEATURE:
<223> OTHER INFORMATION: Primer

<400> SEQUENCE: 36
gcgccctagg aaccatggct ccgcagaacc tga                                33

<210> SEQ ID NO 37
<211> LENGTH: 33
<212> TYPE: DNA
<213> ORGANISM: Artificial sequence
<220> FEATURE:
<223> OTHER INFORMATION: Primer

<400> SEQUENCE: 37
gcgccctagg cactctcaat atccttgcag tcc                                33

<210> SEQ ID NO 38
<211> LENGTH: 32
<212> TYPE: DNA
<213> ORGANISM: Artificial sequence
<220> FEATURE:
<223> OTHER INFORMATION: Primer

<400> SEQUENCE: 38
gcgcggatcc aaagatggcg gcgactctgg ga                                 32

<210> SEQ ID NO 39
<211> LENGTH: 31
<212> TYPE: DNA
<213> ORGANISM: Artificial sequence
<220> FEATURE:
<223> OTHER INFORMATION: Primer

<400> SEQUENCE: 39
gcgcggatcc tcagtagaag cgctttcggc t                                  31

<210> SEQ ID NO 40
<211> LENGTH: 49
```

```
<212> TYPE: DNA
<213> ORGANISM: Artificial sequence
<220> FEATURE:
<223> OTHER INFORMATION: Primer

<400> SEQUENCE: 40
gcgcactagt aaaatgaacg accaaacgca atttacagaa agggctcta          49

<210> SEQ ID NO 41
<211> LENGTH: 46
<212> TYPE: DNA
<213> ORGANISM: Artificial sequence
<220> FEATURE:
<223> OTHER INFORMATION: Primer

<400> SEQUENCE: 41
gcgcactagt taatctaggt catcatcaat ttccatactg tcctca             46

<210> SEQ ID NO 42
<211> LENGTH: 49
<212> TYPE: DNA
<213> ORGANISM: Artificial sequence
<220> FEATURE:
<223> OTHER INFORMATION: Primer

<400> SEQUENCE: 42
gcgccccggg aaaatgaacg accaaacgca atttacagaa agggctcta          49

<210> SEQ ID NO 43
<211> LENGTH: 47
<212> TYPE: DNA
<213> ORGANISM: Artificial sequence
<220> FEATURE:
<223> OTHER INFORMATION: Primer

<400> SEQUENCE: 43
gcgccccggg ttaatctagg tcatcatcaa tttccatact gtcctca            47

<210> SEQ ID NO 44
<211> LENGTH: 34
<212> TYPE: DNA
<213> ORGANISM: Artificial sequence
<220> FEATURE:
<223> OTHER INFORMATION: Primer

<400> SEQUENCE: 44
gcgcggatcc tagagatcat ggaagggaag tggt                          34

<210> SEQ ID NO 45
<211> LENGTH: 36
<212> TYPE: DNA
<213> ORGANISM: Artificial sequence
<220> FEATURE:
<223> OTHER INFORMATION: Primer

<400> SEQUENCE: 45
gcgcggatcc gtttcactct cttcgtggct ttctgt                        36

<210> SEQ ID NO 46
<211> LENGTH: 32
<212> TYPE: DNA
<213> ORGANISM: Artificial sequence
<220> FEATURE:
<223> OTHER INFORMATION: Primer

<400> SEQUENCE: 46
```
cgcgagatct gcctctctac agctcgtcct tg    32

<210> SEQ ID NO 47
<211> LENGTH: 33
<212> TYPE: DNA
<213> ORGANISM: Artificial sequence
<220> FEATURE:
<223> OTHER INFORMATION: Primer

<400> SEQUENCE: 47
gcgcactagt aaaatgcctg aggaagtgca cca    33

<210> SEQ ID NO 48
<211> LENGTH: 32
<212> TYPE: DNA
<213> ORGANISM: Artificial sequence
<220> FEATURE:
<223> OTHER INFORMATION: Primer

<400> SEQUENCE: 48
gcgcactagt aatcgacttc ttccatgcga ga    32

<210> SEQ ID NO 49
<211> LENGTH: 33
<212> TYPE: DNA
<213> ORGANISM: Artificial sequence
<220> FEATURE:
<223> OTHER INFORMATION: Primer

<400> SEQUENCE: 49
gcgcagatct gccatgctgc tatccgtgcc gct    33

<210> SEQ ID NO 50
<211> LENGTH: 19
<212> TYPE: PRT
<213> ORGANISM: Antheraea mylitta

<400> SEQUENCE: 50

Met Arg Val Ile Ala Phe Val Ile Leu Cys Cys Ala Leu Gln Tyr Ala
1               5                   10                  15

Thr Ala Ala

<210> SEQ ID NO 51
<211> LENGTH: 61
<212> TYPE: DNA
<213> ORGANISM: Antheraea mylitta

<400> SEQUENCE: 51
gatcaaaaat gagagtaata gccttcgtca tcttgtgctg cgctttgcag tatgcaactg    60
c    61

<210> SEQ ID NO 52
<211> LENGTH: 61
<212> TYPE: DNA
<213> ORGANISM: Antheraea mylitta

<400> SEQUENCE: 52
ggccgcagtt gcatactgca aagcgcagca caagatcacg aaggctatta ctctcatttt    60
t    61

<210> SEQ ID NO 53
<211> LENGTH: 10
<212> TYPE: PRT

```
<213> ORGANISM: Artificial sequence
<220> FEATURE:
<223> OTHER INFORMATION: Synthetic construct: Polyhistidine-tag

<400> SEQUENCE: 53

Ala Asp His His His His His His Gly Ala
1               5                   10

<210> SEQ ID NO 54
<211> LENGTH: 30
<212> TYPE: DNA
<213> ORGANISM: Artificial sequence
<220> FEATURE:
<223> OTHER INFORMATION: Synthetic construct: Polyhistidine-tag

<400> SEQUENCE: 54
ggccgatcac catcaccacc atcacggagc                                    30

<210> SEQ ID NO 55
<211> LENGTH: 30
<212> TYPE: DNA
<213> ORGANISM: Artificial sequence
<220> FEATURE:
<223> OTHER INFORMATION: Synthetic construct: Polyhistidine-tag

<400> SEQUENCE: 55
ggccgctccg tgatggtggt gatggtgatc                                    30

<210> SEQ ID NO 56
<211> LENGTH: 11
<212> TYPE: PRT
<213> ORGANISM: Artificial sequence
<220> FEATURE:
<223> OTHER INFORMATION: Synthetic construct: Polyhistidine-tag

<400> SEQUENCE: 56

Ala His His His His His His His His Gly Ala
1               5                   10

<210> SEQ ID NO 57
<211> LENGTH: 33
<212> TYPE: DNA
<213> ORGANISM: Artificial sequence
<220> FEATURE:
<223> OTHER INFORMATION: Synthetic construct: Polyhistidine-tag

<400> SEQUENCE: 57
ggcccatcac caccatcacc accatcacgg agc                                33

<210> SEQ ID NO 58
<211> LENGTH: 33
<212> TYPE: DNA
<213> ORGANISM: Artificial sequence
<220> FEATURE:
<223> OTHER INFORMATION: Synthetic construct: Polyhistidine-tag

<400> SEQUENCE: 58
ggccgctccg tgatggtggt gatggtgcac atg                                33

<210> SEQ ID NO 59
<211> LENGTH: 22
<212> TYPE: PRT
<213> ORGANISM: Wasp

<400> SEQUENCE: 59

Met Ser Arg Tyr Ala Leu Ile Val Leu Ile Val Val Val Val Ala Ala
```

```
                                1       5              10             15

Asn Leu Cys Glu Ala Ala
                  20

<210> SEQ ID NO 60
<211> LENGTH: 70
<212> TYPE: DNA
<213> ORGANISM: Wasp

<400> SEQUENCE: 60
gatcaaaaat gagtcgttac gctctaattg tgctcatcgt cgtggtggtc gcggcgaact          60
tatgcgaagc                                                                70

<210> SEQ ID NO 61
<211> LENGTH: 70
<212> TYPE: DNA
<213> ORGANISM: Wasp

<400> SEQUENCE: 61
ggccgcttcg cataagttcg ccgcgaccac cacgacgatg agcacaatta gagcctaacg          60
actcattttt                                                                70
```